United States Patent
Nakata et al.

(10) Patent No.: US 6,576,559 B2
(45) Date of Patent: *Jun. 10, 2003

(54) SEMICONDUCTOR MANUFACTURING METHODS, PLASMA PROCESSING METHODS AND PLASMA PROCESSING APPARATUSES

(75) Inventors: Toshihiko Nakata, Hiratsuka (JP); Takanori Ninomiya, Hiratsuka (JP); Sachio Uto, Yokohama (JP); Hiroyuki Nakano, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/095,066

(22) Filed: Mar. 12, 2002

(65) Prior Publication Data
US 2002/0094685 A1 Jul. 18, 2002

Related U.S. Application Data

(63) Continuation of application No. 09/260,074, filed on Mar. 2, 1999, now Pat. No. 6,355,570.

(30) Foreign Application Priority Data

Mar. 4, 1998 (JP) .......................................... 10-052088

(51) Int. Cl.[7] ............................................. H01L 21/302
(52) U.S. Cl. ....................... 438/706; 438/709; 438/710; 438/712; 438/714
(58) Field of Search .................... 438/706, 710–714, 438/709; 118/723 E, 723 MA; 356/336, 430, 431; 250/559.41

(56) References Cited

U.S. PATENT DOCUMENTS 4,865,445 A * 9/1989 Kuriyama et al. ............. 356/73
5,030,842 A * 7/1991 Koshinaka et al. ..... 250/559.41
5,343,290 A * 8/1994 Batchelder et al. .......... 356/484

(List continued on next page.)

FOREIGN PATENT DOCUMENTS

| JP | 57-118630 | 7/1982 |
|---|---|---|
| JP | 6371633 | 4/1988 |
| JP | 3-25355 | 2/1991 |
| JP | 3-147317 | 6/1991 |
| JP | 4-74857 | 11/1992 |
| JP | 6-82358 | 3/1994 |
| JP | 6-124902 | 5/1994 |
| JP | 07-012707 | 1/1995 |
| JP | 9-260358 | 10/1997 |
| JP | 10-213539 | 8/1998 |

*Primary Examiner*—Benjamin L. Utech
*Assistant Examiner*—Duy-Vu Deo
(74) *Attorney, Agent, or Firm*—Antonelli, Terry, Stout & Kraus, LLP

(57) ABSTRACT

The present invention provides a semiconductor manufacturing method, a plasma processing method and a plasma processing apparatus for generating a plasma in a processing chamber and carrying out processing on material to be processed by using the plasma, comprising a floating-foreign-particle measuring apparatus including: a light radiating optical system for radiating a light having a desired wavelength and completing intensity modulation at a desired frequency to the processing chamber; a scattered-light detecting optical system for separating a component with the desired wavelength from scattered lights obtained from the processing chamber as a result of radiation of the light by the light radiating optical system, for optically receiving the component and for converting the component into a first signal; and a foreign-particle-signal extracting unit which separates a second signal representing foreign particle floating in the plasma or in an area in proximity to the plasma from a third signal obtained by emission of the plasma for detection of the second signal by extraction of a component with the desired frequency used for the intensity modulation from the first signal obtained from the scattered-light detecting optical system.

22 Claims, 17 Drawing Sheets

U.S. PATENT DOCUMENTS

| | | | | |
|---|---|---|---|---|
| 5,448,364 A | * | 9/1995 | Moran | 356/430 |
| 5,552,016 A | | 9/1996 | Ghanayem | 156/345 |
| 5,861,952 A | * | 1/1999 | Tsuji et al. | 356/349 |
| 5,885,472 A | | 3/1999 | Miyazaki et al. | 438/9 |
| 5,888,337 A | | 3/1999 | Saito | 156/345 |
| 5,936,726 A | | 8/1999 | Takeda et al. | 356/237.2 |
| 5,943,130 A | * | 8/1999 | Bonin et al. | 356/336 |
| 6,355,570 B1 | * | 3/2002 | Nakata et al. | 438/706 |

* cited by examiner

SEMICONDUCTOR MANUFACTURING METHODS, PLASMA PROCESSING METHODS AND PLASMA PROCESSING APPARATUSES

This is a continuation of parent application Ser. No. 09/260,074, filed Mar. 2, 1999, U.S. Pat. No. 6,355,570 the entire disclosure of which is hereby incorporated by reference.

BACKGROUND OF THE INVENTION

The present invention relates to semiconductor manufacturing methods, plasma processing methods and plasma processing apparatuses for increasing the yield of material to be processed such as a semiconductor substrate by in-situ (on-the-spot) measuring sub-micron foreign particles floating in the course of processing in a plasma processing chamber without being affected external disturbances such as plasma emitted light.

Prior arts for monitoring foreign particles floating in a plasma processing chamber are disclosed in several documents. In the following description, prior arts disclosed in Japanese Patent Laid-open Nos. Sho 57-118630, Hei 3-25355, Hei 3-147317, Hei 6-82358 and Hei 6-124902 are referred to as prior arts 1 to 5 respectively.

Prior art 1 cited above introduces a depositing apparatus which comprises a means for radiating parallel lights in a reaction space wherein the parallel lights have a spectrum different from the spectrum of a light self emitted in the reaction space and a means for detecting lights scattered from infinitesimal particles generated in the reaction space due to radiation of the parallel lights.

Prior art 2 cited above introduces an infinitesimal-particle measuring apparatus for measuring floating infinitesimal particles and infinitesimal particles stuck to the surface of a semiconductor substrate for making semiconductor devices by using a scattering phenomenon of laser beams. The infinitesimal-particle measuring apparatus comprises: a laser-beam-phase modulating unit for generating 2 laser beams having equal wavelengths and a difference in phase modulated at a predetermined frequency; an optical system for directing the 2 laser beams to intersect each other in a space containing infinitesimal particles being measured; a light detecting unit for receiving lights scattered by the infinitesimal particles being measured in an area where the 2 laser beams intersect each other and converting the received lights into an electrical signal; and a signal processing unit for extracting a signal component having a frequency equal to the frequency of a phase modulation signal used in the laser-beam-phase modulating unit or a frequency twice the frequency of the phase modulation signal and a difference in phase from the phase modulation signal unchanged with the lapse of time out off the electrical signal representing the scattered lights.

Prior art 3 cited above is a technology for measuring the degree of pollution in a reactor by analyzing scattered lights. The art includes the steps of: a scanning operation by using a radiated coherent light to generate lights scattered in the reactor on the spot; and detecting the lights scattered in the reactor.

Prior art 4 cited above introduces a particle detecting apparatus which comprises: a laser means for generating a laser beam; a scanner means for scanning an area in a reactor chamber of a plasma processing tool including particles to be measured by using the laser beam; a video camera means for generating a video signal representing laser beams scattered by particles in the area; and a means for processing the video signal and displaying an image of the video signal.

Prior art 5 cited above introduces a plasma processing apparatus which comprises: a camera apparatus for observing a plasma generation area in a plasma processing chamber; a data processing unit for obtaining desired information by processing a picture taken by the camera apparatus; an exhaust means for reducing the number of particles by using the information produced by the data processing apparatus; and a control unit for controlling at least one of a process-gas introducing means, a high-frequency-voltage applying means and a purge-gas introducing means.

Referred to as prior art 6, an infinitesimal-particle measuring apparatus used in control of advanced cleaning processes such as semiconductor manufacturing processes and chemical manufacturing processes is disclosed in Japanese Patent Laid-open No. Sho 63-71633. Used for detecting scattered lights from particles in a liquid sample due to radiation of a laser beam to an infinitesimal area of a container flowing the liquid sample being examined, the infinitesimal-particle measuring apparatus provided by prior art 6 comprises: a means for carrying out intensity modulation on the laser beam at a fixed frequency; and a phase detector for measuring a signal coming from a detector having a frequency equal to the frequency of the intensity modulation.

In the plasma processing apparatus, a substance generated by a reaction occurring in a plasma process is deposited on the surface wall of the plasma processing chamber or an electrode. With the lapse of time, however, such a substance is peeled off, becoming a floating infinitesimal foreign particle. The floating infinitesimal foreign particle is stuck to a material to be processed in the course of plasma processing, resulting in a bad product. In other cases, the floating infinitesimal foreign particle is trapped on a bulk-sheath boundary surface and falls on the material to be processed at the time a plasma discharging phenomenon is terminated at the end of the plasma processing. The foreign particle stuck to the material to be processed gives rise to a poor characteristic and an appearance defect. As a result, such a substance decreases the yield of materials to be processed such as semiconductor substrates.

In the mean time, the degree of integration of circuit patterns created on a material to be processed such as a semiconductor substrate has been becoming higher and higher. In the semiconductor field, for example, the integration of circuit patterns in the DRAM is under way, increasing the capacity of the DRAM to 256 Mbit and even to 1 Gbit. That is to say, the minimum line width of the circuit patterns is in a process of being miniaturized to a size in the range 0.25 to 0.18 $\mu$m. It thus becomes necessary to also measure infinitesimal foreign particles on the order of down to sub-microns which float in the plasma or in an area in proximity to the plasma.

Thus, required in the plasma processing apparatus is a capability of measuring also the infinitesimal foreign particles of the order of down to sub-microns floating in the plasma or in an area in proximity to the plasma without being affected by an external disturbance such as plasma emitted light. Since the plasma emitted light exhibits a continuous wavelength spectrum over a range from a zone beyond the ultraviolet ray to a zone beyond the near-infrared ray, however, it is difficult to separate infinitesimal foreign particles of the order of down to sub-microns floating in the plasma or in an area in proximity to the plasma from the plasma emitted light in order to detect the foreign particles by using the spectrum generated in accordance with prior art 1.

As described above, in either of prior arts 1 to 5, there is no consideration of a matter regarding an attempt to separate very weak scattered lights generated by infinitesimal foreign particles on the order of down to sub-microns floating in the plasma or in an area in proximity to the plasma from the plasma emitted light in order to detect the scattered lights.

In addition, in prior art 6 used for measuring the number of particles in a liquid sample flowing to a container, there is also no consideration of a matter regarding an attempt to separate very weak scattered lights generated by infinitesimal foreign particles of the order of down to sub-microns floating in the plasma or in an area in proximity to the plasma from the plasma emitted light in order to detect only the scattered lights.

SUMMARY OF THE INVENTION

It is thus an object of the present invention addressing the problems described above to provide a plasma processing method and a plasma processing apparatus for improving the yield of materials to be processed by enabling real-time monitoring of a state of pollution in a plasma processing chamber through substantial enhancement of the detection sensitivity to detect infinitesimal foreign particles on the order of down to sub-microns floating in the plasma or in an area in proximity to the plasma in the course of plasma processing in the plasma processing chamber by separating the light scattered by the foreign particles from a plasma emitted light.

It is another object of the present invention to provide a semiconductor manufacturing method which allows a semiconductor device with a high quality to be manufactured at a high yield by enabling real-time monitoring of a state of pollution in a plasma processing chamber through substantial enhancement of the detection sensitivity to detect infinitesimal foreign particles on the order of down to sub-microns floating in the plasma or in an area in proximity to the plasma in the plasma processing chamber by separating the light scattered by the foreign particle from a plasma emitted light.

By the way, in order to achieve the objects described above, the present invention provides a semiconductor manufacturing method for manufacturing a semiconductor by generating a plasma in a processing chamber and carrying out processing on a semiconductor substrate by using the plasma, comprising the steps of:

preparing a floating-foreign-particle measuring apparatus including a light radiating optical system for radiating a light having a desired wavelength and completing intensity modulation at a desired frequency to the processing chamber; a scattered-light detecting optical system for separating a component with the desired wavelength from scattered lights obtained from the processing chamber as a result of radiation of the light by the light radiating optical system, for optically receiving the component and for converting the component into a first signal; and a foreign-particle-signal extracting unit (means) which separates a second signal representing foreign particle floating in the plasma or in an area in proximity to the plasma from a third signal obtained by emission of the plasma for detection of the second signal by extraction of a component with the desired frequency used for the intensity modulation from the first electrical signal obtained from the scattered-light detecting optical system; and measuring foreign particle floating in the plasma or the area on base of said second electrical signal being detected from said foreign-particle-signal extracting unit by using the floating-foreign-particle measuring apparatus.

In addition, the present invention also provides a plasma processing method for generating a plasma in a processing chamber and carrying out processing on material to be processed by using the plasma, comprising the steps of:

preparing a floating-foreign-particle measuring apparatus including a light radiating optical system for radiating a light having a desired wavelength and completing intensity modulation at a desired frequency to the processing chamber; a scattered-light detecting optical system for separating a component with the desired wavelength from scattered lights obtained from the processing chamber as a result of radiation of the light by the light radiating optical system, for optically receiving the component and for converting the component into a first signal; and a foreign-particle-signal extracting unit (means) which separates a second signal representing foreign particle floating in the plasma or in an area in proximity to the plasma from a third signal obtained by emission of the plasma for detection of the second signal by extraction of a component with the desired frequency used for the intensity modulation from the first signal obtained from the scattered-light detecting optical system; and measuring foreign particle floating in the plasma or the area on base of said second signal being detected from said foreign-particle-signal extracting unit by using the floating-foreign-particle measuring apparatus.

Furthermore, the present invention also provides a plasma processing apparatus for generating a plasma in a processing chamber and carrying out processing on material to be processed by using the plasma, comprising a floating-foreign-particle measuring apparatus including:

a light radiating optical system for radiating a light having a desired wavelength and completing intensity modulation at a desired frequency to the processing chamber;

a scattered-light detecting optical system for separating a component with the desired wavelength from scattered lights obtained from the processing chamber as a result of radiation of the light by the light radiating optical system, for optically receiving the component and for converting the component into a signal; and a foreign-particle-signal extracting unit (means) for separating a signal representing foreign particle floating in the plasma or in an area in proximity to the plasma from that emitted by the plasma for detection of the signal representing the foreign particle by extraction of a component with the desired frequency used by the intensity modulation from the signal obtained from the scattered-light detecting optical system.

Moreover, the present invention also provides a plasma processing apparatus for generating a plasma in a processing chamber and carrying out processing on material to be processed by using the plasma, comprising a floating-foreign-particle measuring apparatus including:

a light radiating optical system for radiating a light having a desired wavelength and completing intensity modulation at a desired frequency to the processing chamber;

a back-scattered light detecting optical system for separating a component with the desired wavelength from back-scattered lights obtained from the processing chamber as a result of radiation of the light by the light radiating optical system, for optically receiving the component and for converting the component into a first signal; and a foreign-particle-signal extracting unit (means) which separates a second signal representing foreign particle floating in the plasma or in an area in proximity to the plasma from a third signal obtained by emission of the plasma for detection of the second signal by extraction of a component with the desired frequency used for the intensity modulation from the first signal obtained from the back-scattered light detecting optical system.

In the light radiating optical system provided by the present invention, an excitation frequency or an emission frequency of the plasma varies to a certain degree. Taking such variations into consideration, the frequency used in the intensity modulation is set at a value which deviates from the excitation or emission frequency of the plasma and a high-order harmonic frequency of the excitation or emission frequency by at least a difference in the range 10 to 15%.

Moreover, according to the present invention, an ion acceleration frequency and the frequency of a radio-frequency power supply for generating a voltage applied to a electrode on which a material to be processed is set are also included in the excitation or emission frequency of the plasma.

In addition, in the light radiating optical system provided by the present invention, a signal used in the intensity modulation has a rectangular waveform with a duty in the range 40 to 60%.

Furthermore, the back-scattered light detecting optical system provided by the present invention has a light shielding optical element for shielding a specular reflection light coming from the processing chamber.

Moreover, the light radiating optical system provided by the present invention has a scanning system for scanning the light across a surface of the material to be processed.

Moreover, the intensity-modulation frequency used in the light radiating optical system provided by the present invention is between the excitation or emission frequency of the plasma and a frequency of a direct-current component.

In addition, according to the present invention, there are provided:

an observation window provided on the processing chamber and used for transmitting the light radiated by the light radiating optical system and the scattered lights obtained from the processing chamber; and a generated-substance-deposition preventing unit (means) provided in the processing chamber and used for preventing a generated substance from being deposited on an inner surface of the observation window.

Furthermore, the light radiating optical system employed in the plasma processing apparatus provided by the present invention has an optical system for converting a beam radiated to the processing chamber into a diffractionless beam or a Bessel beam.

Moreover, the light radiating optical system provided by the present invention has a configuration in which the diffractionless beam or the Bessel beam is formed only in a surface direction of a surface of the material to be processed so as to allow foreign particle floating in an area on a plasma bulk-sheath boundary surface to be detected.

Moreover, the light radiating optical system provided by the present invention has a configuration in which the diffractionless beam is generated by an axicon or an annular aperture optical system.

In addition, the light radiating optical system provided by the present invention has a configuration for radiating linear-polarization illumination light.

Furthermore, the back-scattered light detecting optical system employed in the plasma processing apparatus provided by the present invention has a polarization optical system for detecting backward-direction scattered lights coming from foreign particle floating in a plasma or in an area in proximity to the plasma.

Moreover, the present invention provides a semiconductor manufacturing method comprising:

a film-formation step of measuring foreign particle floating in a first plasma generated in a first processing chamber or a first area in proximity to the first plasma, while generating the first plasma in the first processing chamber and forming a film on a semiconductor substrate by using the first plasma, by using a first floating-foreign-particle measuring apparatus including: a first light radiating optical system for radiating a light having a desired wavelength and completing intensity modulation at a desired frequency to the first processing chamber; a first scattered-light detecting optical system for separating a component with the desired wavelength from scattered lights obtained from the first processing chamber as a result of radiation of the light by the first light radiating optical system, for optically receiving the component and for converting the component into a first signal; and a first foreign-particle-signal extracting unit (means) which separates a second signal representing foreign particle floating in the first plasma or in the area from a third signal obtained by emission of the first plasma for detection of the second signal by extraction of a component with the desired frequency used for the intensity modulation from the first signal obtained from the first scattered-light detecting optical system; and an etching step of measuring foreign particle floating in a second plasma generated in a second processing chamber or foreign particle floating in a second area in proximity to the second plasma, while generating the second plasma in the second processing chamber and carrying out an etching process on a semiconductor substrate subjected to film formation by using the second plasma, by using a second floating-foreign-particle measuring apparatus including: a second light radiating optical system for radiating a light having a desired wavelength and completing intensity modulation at a desired frequency to the second processing chamber; a second scattered-light detecting optical system for separating a component with the desired wavelength from scattered lights obtained from the second processing chamber as a result of radiation of the light by the second light radiating optical system, for optically receiving the component and for converting the component into a forth signal; and a second foreign-particle-signal extracting unit (means) which separates a fifth signal representing foreign particle floating in the second plasma or in the area from a sixth signal obtained by emission of the second plasma for detection of the fifth signal by extraction of a component with the desired frequency used by the intensity modulation from the forth signal obtained from the second scattered-light detecting optical system.

As described above, the semiconductor manufacturing method provided by the present invention includes a film-formation process and an etching process.

According to the configurations described above, the detection sensitivity to detect infinitesimal foreign particle on the order of down to sub-microns floating in a plasma or in an area in proximity to the plasma can be increased substantially by separation of weak scattered lights generated by the infinitesimal foreign particle from a plasma emitted light for a detection purpose. As a result, it is possible to carry out real-time monitoring of a state of pollution in a plasma processing chamber and to reduce the number of inadvertently produced bad products due to foreign particle stuck thereto, allowing semiconductor devices with a high quality to be manufactured at a high yield.

In addition, according to the configurations described above, by using a diffractionless beam, uniform radiation of energy and detection at a uniform sensitivity can be implemented over the entire surface of a material to be processed. Moreover, by separating weak scattered lights generated by infinitesimal foreign particle on the order of down to sub-microns floating in the plasma or in an area in proximity to the plasma from a plasma emitted light for a detection purpose, the infinitesimal foreign particle on the order of down to sub-microns floating in the plasma or in an area in proximity to the plasma can be detected with a high degree of stability and at a substantially increased detection sensitivity over the entire surface of a material to be processed. As a result, it is possible to carry out real-time monitoring of the state of pollution in the plasma processing chamber.

Furthermore, according to the configurations described above, by separation of weak back-scattered lights generated from the infinitesimal foreign particle on the order of down to sub-microns floating in the plasma or in an area in proximity to the plasma from a plasma emitted light for a detection purpose, an observation window can be prevented against dirt with ease, a laser radiating optical system as well as a scattered-light detecting optical system can be made compact and the detection sensitivity to detect infinitesimal foreign particles on the order of down to sub-microns floating in the plasma or in an area in proximity to the plasma can be increased substantially. As a result, it is possible to carry out real-time monitoring of a state of pollution in a plasma processing chamber.

DETAILED DESCRIPTION OF THE PREFERRED EMBODIMENTS

The following is a description of embodiments implementing semiconductor manufacturing methods and semiconductor manufacturing apparatuses provided by the present invention for manufacturing products such as semiconductor devices with a high quality through reduction of the number of bad substrates to be processed or bad materials to be processed caused by stuck foreign particle by enabling real-time monitoring of a state of pollution in a plasma processing chamber with reference to accompanying diagrams.

Processing apparatus for manufacturing products such as semiconductor devices includes a plasma etching apparatus and a plasma film-formation apparatus. These processing apparatuses generate a plasma in a plasma processing chamber, carry out an etching process on a substrate to be processed and create films by using CVD and sputtering methods.

The following is a description of embodiments for monitoring a state of pollution in a real-time manner, that is, for monitoring a state of generation of foreign particle, in a plasma processing chamber of the processing apparatus with reference to FIGS. 1 to 20.

Figure 1:
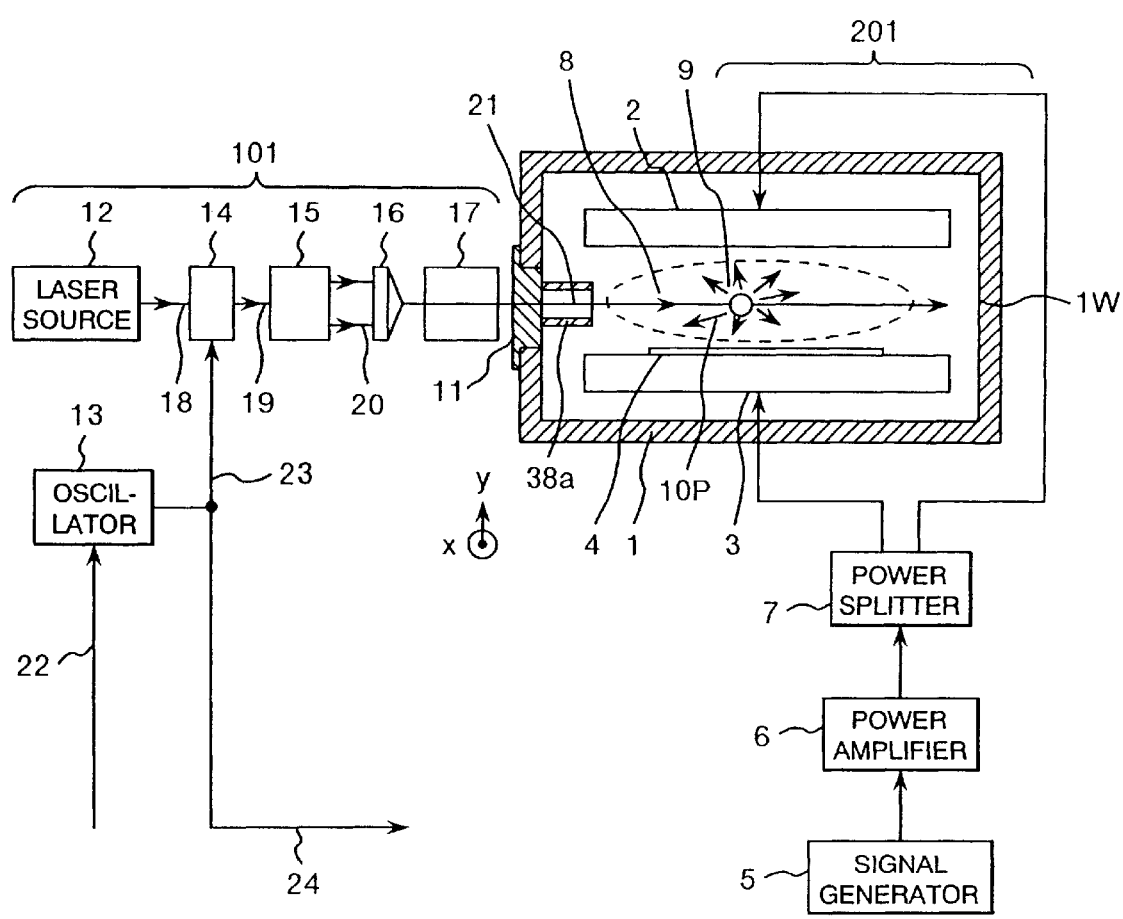
FIG. 1 is a diagram showing a front view of a first embodiment implementing a floating-foreign-particle measuring apparatus employed in a plasma processing apparatus provided by the present invention.

First of all, a plasma processing apparatus provided by the present invention is explained by referring to FIG. 1. As shown in FIG. 1, the plasma processing apparatus 201 generates a plasma 8 between an electrode 2 and an electrode 3 for mounting a substrate 4 to be processed (a material to be processed) and processes the substrate 4 by using the plasma 8. In the plasma processing apparatus 201, during the time the plasma processing is carried out on the substrate 4, a substance generated by a reaction is not all exhausted. Instead, some of the substance is deposited on the surface of the wall of a plasma processing chamber 1 or on the electrode 2 and 3. Furthermore, in accordance with the number of substrates to be processed by the plasma processing is increased in a plasma processing chamber 1, much of the substance deposited on the surface of the wall of a plasma processing chamber 1 or on the electrode 2 and 3 is peeled off, floating in the plasma processing chamber 1. Then, the floating substance, that is a foreign particle, penetrates into the plasma 8 and lots of the foreign particle are stuck to the surface of the substrate 4. As a result, a bad substrate 4 to be processed with lots of foreign particle stuck thereto is inadvertently produced.

In particular, in a semiconductor field wherein high integration of circuit patterns formed on the substrate 4 is in progress, miniaturization to reduce the minimum wire width of the circuit patterns to a value in the range 0.25 to 0.18 $\mu$m is under way. Unfortunately, however, the plasma processing apparatus may inadvertently result in production of a bad substrate 4 to be processed, to the surface of which foreign particle having a size on the order of even sub-microns are stuck.

The following is a description of a parallel-plate plasma etching apparatus, a sort of plasma etching apparatus 94 used as a plasma processing apparatus, is explained by referring to FIG. 1. An upper electrode 2 and the lower electrode 3 parallel to each other are provided in the plasma processing chamber 1, sandwiching a gap wherein the plasma 8 is generated by the two electrodes 2 and 3. The substrate 4 is placed on the lower electrode 3. By the way, gas for an etching process is supplied from an external source to the gap between the upper and lower electrodes 2 and 3 in the plasma processing chamber. A voltage output by a power amplifier 6 is modulated by a signal having a high frequency generated by a signal generator 5. The modulated high-frequency voltage having a frequency in the range 380 to 800 kHz is divided by a power splitter 7, being applied across the gap between the upper and lower electrodes 2 and 3. As a result, a discharge phenomenon occurring between the upper and lower electrodes 2 and 3 converts the supplied gas for an etching process into a plasma 8. The activated state of the generated plasma 8 is used for etching the substrate 4. Furthermore, an etching-process apparatus monitors the state of progress of the etching process, detecting the end point of the process as accurately as possible. As a result, the etching process is carried out to produce a predetermined pattern shape and a predetermined depth. That is to say, as the end point is detected, the output of the power amplifier 6 is removed and, then, the substrate 4 is taken out from the plasma processing chamber 1.

In addition, there is also a plasma etching apparatus 94 which is used for generating a plasma using a magnetic or electric field by introduction of a resonant microwave and used for utilizing the plasma for an etching process.

In a plasma film forming apparatus 90, CVD gas is supplied typically from the upper electrode, being converted into a plasma, generated by using high frequency electric power, which is then put in a reaction to create a film on the substrate.

Figure 3:
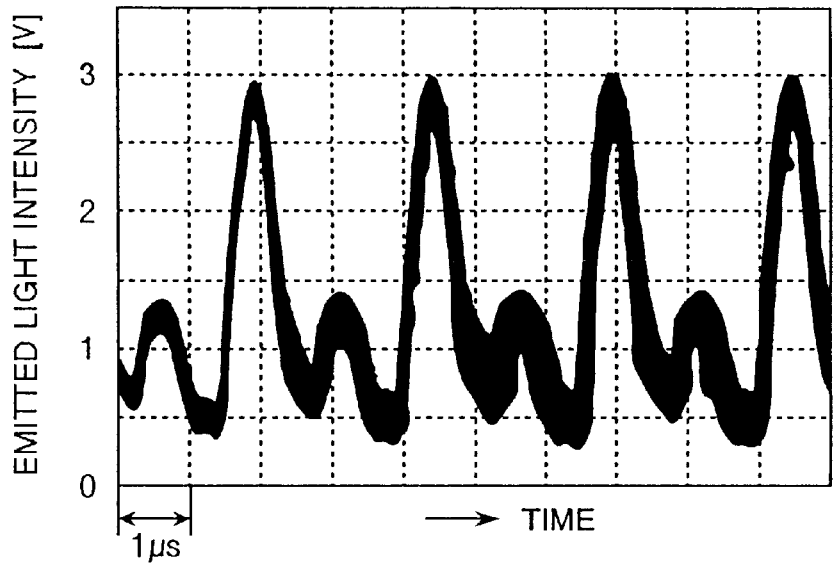
FIG. 3 is a picture showing a waveform of a plasma emitted light.
Figure 4:
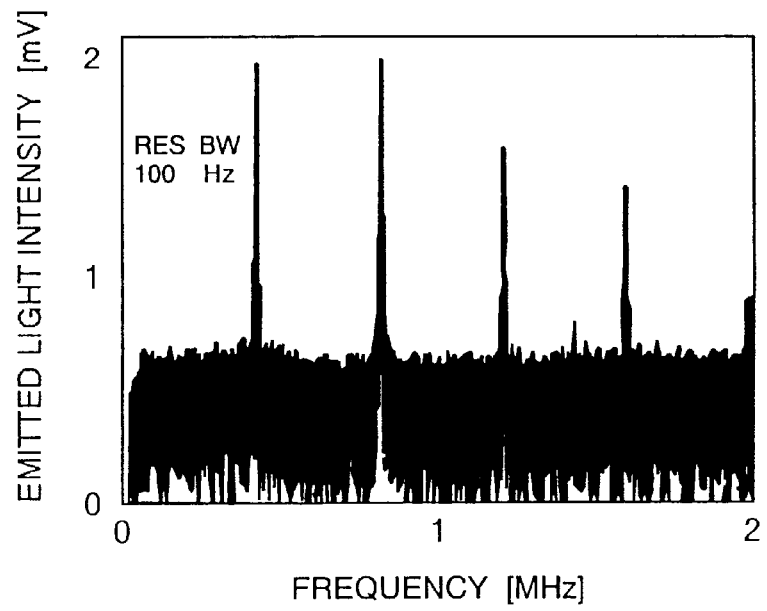
FIG. 4 is a picture showing a frequency spectrum of a plasma emitted light observed by using a spectrum analyzer.
Figure 5:
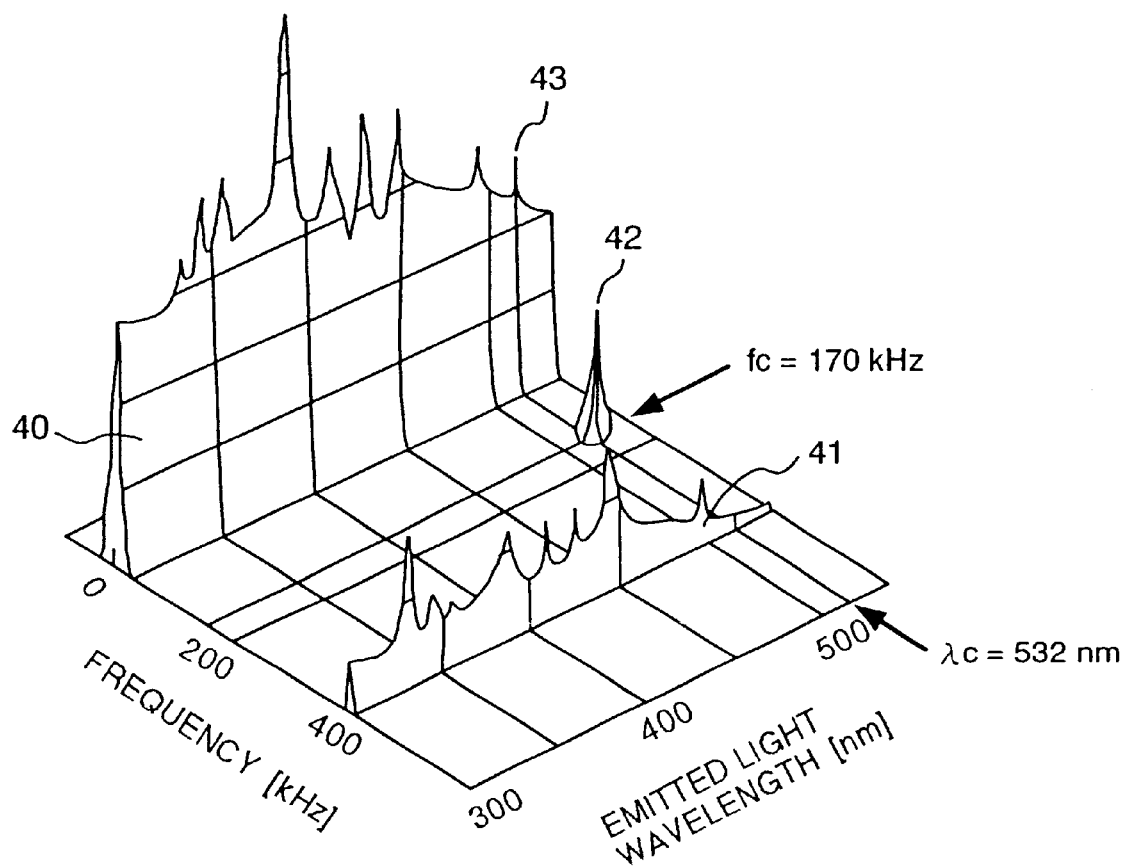
FIG. 5 is a diagram showing a state of separation of the light scattered by the foreign particle from a plasma emitted light in the wavelength and the frequency of domain.

Next, the basic principle of the floating-foreign-particle measuring apparatus 301 provided by the present invention is explained by referring to FIGS. 3 to 5. The floating-foreign-particle measuring apparatus is used when it is necessary to measure the amount of foreign particles floating in the plasma 8 generated by the plasma processing apparatus or in an area in proximity to the plasma. FIG. 3 is a picture showing typical changes in waveform of a plasma emitted light with time obtained as a result of observation in an etching process with the plasma excitation frequency set at 400 kHz. To be more specific, the figure shows changes in emitted-light intensity [V] with time where the symbol V represents the voltage unit 'volt'. As shown in FIG. 3, the intensity [V] of the plasma emitted light can be judged to change periodically in synchronization with the plasma excitation frequency of 400 kHz generated by a signal generator 5 in FIG. 1. FIG. 4 is a picture showing typical frequency spectrum of a plasma emitted light obtained as a result of observation by means of a spectrum analyzer. To be more specific, the picture shows the fundamental frequency component of 400 kHz and the high-order harmonic frequency component of 800 kHz, 1,200 kHz and 1,600 kHz. FIG. 5 is a diagram showing both frequency spectra and wavelength spectra of the plasma emitted light shown in FIG. 4. The diagram also shows both a frequency spectrum and a wavelength spectrum of scattered lights from floating foreign particles in the plasma when a radiated laser beam having a wavelength of 532 nm or having a green color is subjected to intensity modulation at a frequency of 170 kHz. To put in detail, FIG. 5 shows that, at a plasma excitation frequency of 400 kHz the frequency components of the plasma emitted light are composed of a direct current component 40, a 400 kHz component 41, and so on. That is to say, each frequency component of the plasma emitted light exist discretely. Thus, there is a free zone in the frequency domain. As is also obvious from the figure, from the plasma 8 generated on the substrate 4, light with a variety of wavelength components is emitted and radiated to floating foreign particle on the order of down to sub-microns. The wavelength components range from a deep-ultraviolet ray with a wavelength of about 200 nm to a near-infrared ray with a wavelength of about 700 nm.

Thus, for example, by executing the steps of carrying out intensity modulation on a laser beam having a wavelength of 532 nm or a green color at a typical frequency of 170 kHz which is different from the frequency of the plasma emitted light, radiating the intensity-modulated laser beam into the plasma processing chamber 1 and extracting only a peak 42 with the frequency of 170 kHz and the wavelength of 532 nm from a detected light, scattered lights from foreign particle on the order of down to sub-microns can be separated for a detection purpose from the plasma emitted light. By extracting both the wavelength component of the radiated laser beam and the frequency component experiencing the intensity modulation from the detected light as described above, scattered lights from foreign particle on the order of down to sub-microns can be separated and detected from the plasma emitted light which includes a variety of frequency components and a variety of wavelength components. By the way, the wavelength of the radiated laser beam can be set at any value in the range 200 nm (a short wavelength of the deep-ultraviolet ray) to 700 nm (a long wavelength of the near-infrared ray) allowing a plasma to be emitted including a relatively large wavelength of the infrared ray. In order to increase the intensity of scattered lights coming from foreign particle on the order of down to sub-microns, however, it is desirable to set the wavelength of the radiated laser beam at a value shorter than the green color such as the wavelength of the violet or ultraviolet ray. In this way, even if a laser beam with same wavelength as that of plasma emitted light is radiated, by extracting both the wavelength component of the radiated laser beam and the frequency component experiencing the intensity modulation from the detected light, scattered lights coming from foreign particles on the order of down to sub-microns can be separated for a detection purpose from the plasma emitted light which includes noise components.

The following is a description of a first embodiment implementing the floating-foreign-particle measuring apparatus 301 provided by the present invention and used for measuring foreign particle floating in the plasma or in an area in proximity to the plasma. The floating-foreign-particle measuring apparatus 301 comprises the laser radiating optical system 101 shown in FIG. 1, the scattered-light detecting optical system 102 shown in FIG. 2 and a signal processing control system 103 also shown in FIG. 2.

Figure 6A:
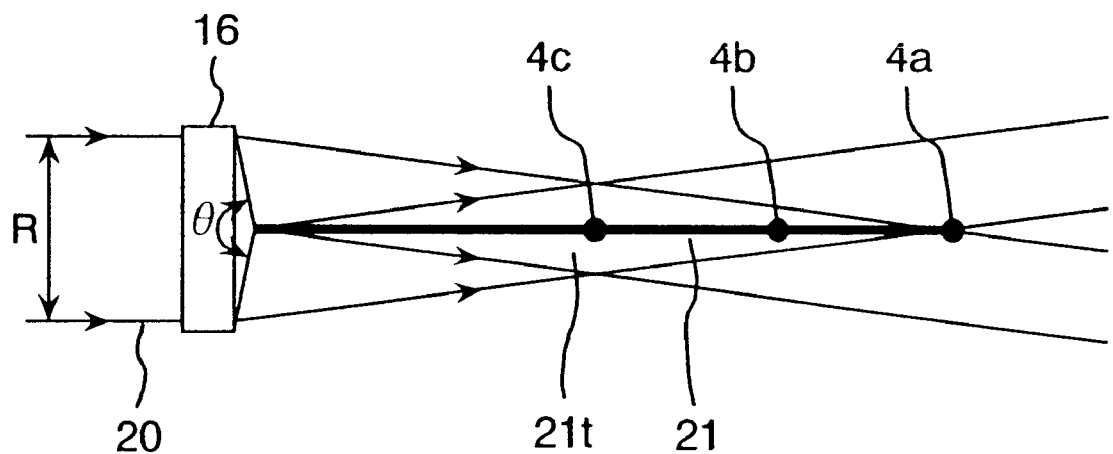
FIG. 6A is a diagram showing a front view of a state of generation of a diffractionless beam by an axicon.
Figure 6B:
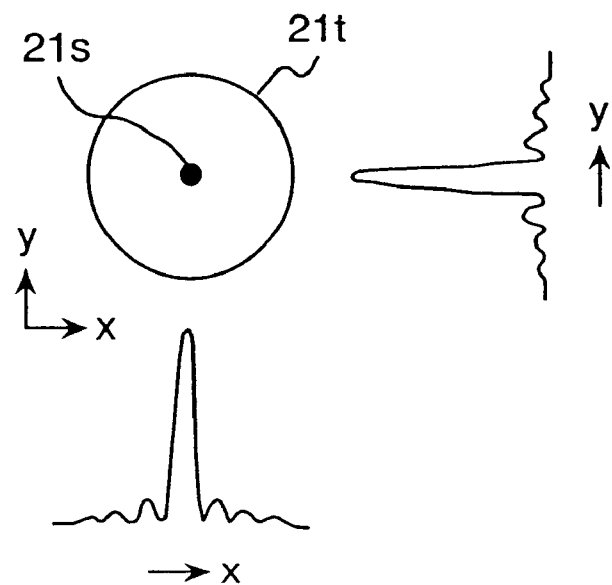
FIG. 6B is a diagram showing an intensity distribution of the diffractionless beam on a 21$t$ surface which is generated by the axicon.
Figure 8:
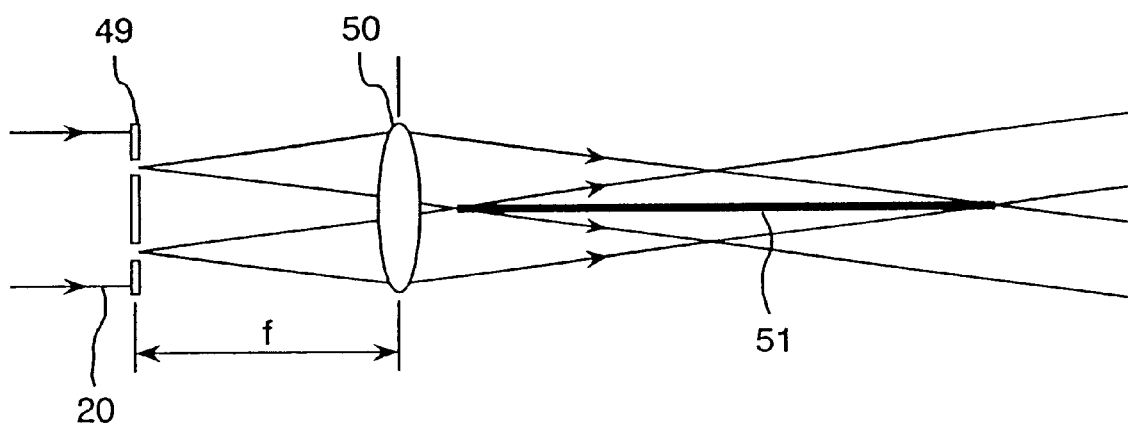
FIG. 8 is a diagram showing generation of a diffractionless beam by an annular aperture optical system.

In the laser radiating optical system 101, first of all, an S-polarization beam 18 generated by a laser source 12 is supplied to an intensity modulator 14. The laser source 12 includes a solid laser with a wavelength of 532 nm, a He—Ne laser with a wavelength of 633 nm, an Ar laser with a wavelength of 514.5 nm and a semiconductor laser beam with a wavelength of 780 nm. The solid laser is excited by a semiconductor laser. The intensity modulator 14 can be implemented typically by an AO (Acousto-Optical) modulator or a mechanical intensity modulator which rotates a disc having an aperture at a high rotational speed. A rectangular-waveform signal 24 with a duty in the range 40 to 60% and a typical frequency of 170 kHz different from the frequency of the plasma emitted light is output by an oscillator 13 in accordance with a control signal 22 generated by a computer 33 and applied to the AO modulator which is used as the intensity modulator 14. Thus, the S-polarization beam 18 supplied to the intensity modulator 14 is subjected to intensity modulation at this frequency. A beam 19 completing the intensity modulation is expanded by a beam expander 15 and an expanded beam 20 is then converted into a diffractionless beam 21 referred to as a 0-order Bessel beam by a conical prism referred to as an axicon 16. As shown in FIGS. 6A and 6B, the diffractionless beam 21 has a very large depth of focus. In this first embodiment, by adjusting the vertex angle θ of the cone of the axicon 16 and the diameter R of the incident beam 20, it is possible to implement an optical system which is capable of sustaining a spot 21s with a diameter in the range about 10 to 30 μm around a depth of focus of about 300 mm. It should be noted that notation 20t denotes a side robe surrounding the central spot 21s. As a result, it is possible to radiate foreign particle at a uniform energy density to the center 4b and the ends 4a and 4c of the substrate 4 which are aligned along the optical axis. It is also worth noting that, as shown in FIG. 8, the parallel beams 20 hit an annual aperture 49 and emanate from it. Then, by carrying out optical Fourier transform on the emanating beams by means of a lens 50 located at the focal distance f, the same diffractionless beam 51 can also be obtained as well.

In addition, instead of employing the axicon 16, a beam having a laser power in the range 2 to 5 W can also be introduced as it is without converging the beam. In this case, a lens having a long focal length f of about 300 mm is employed as a beam converging lens.

Figure 2:
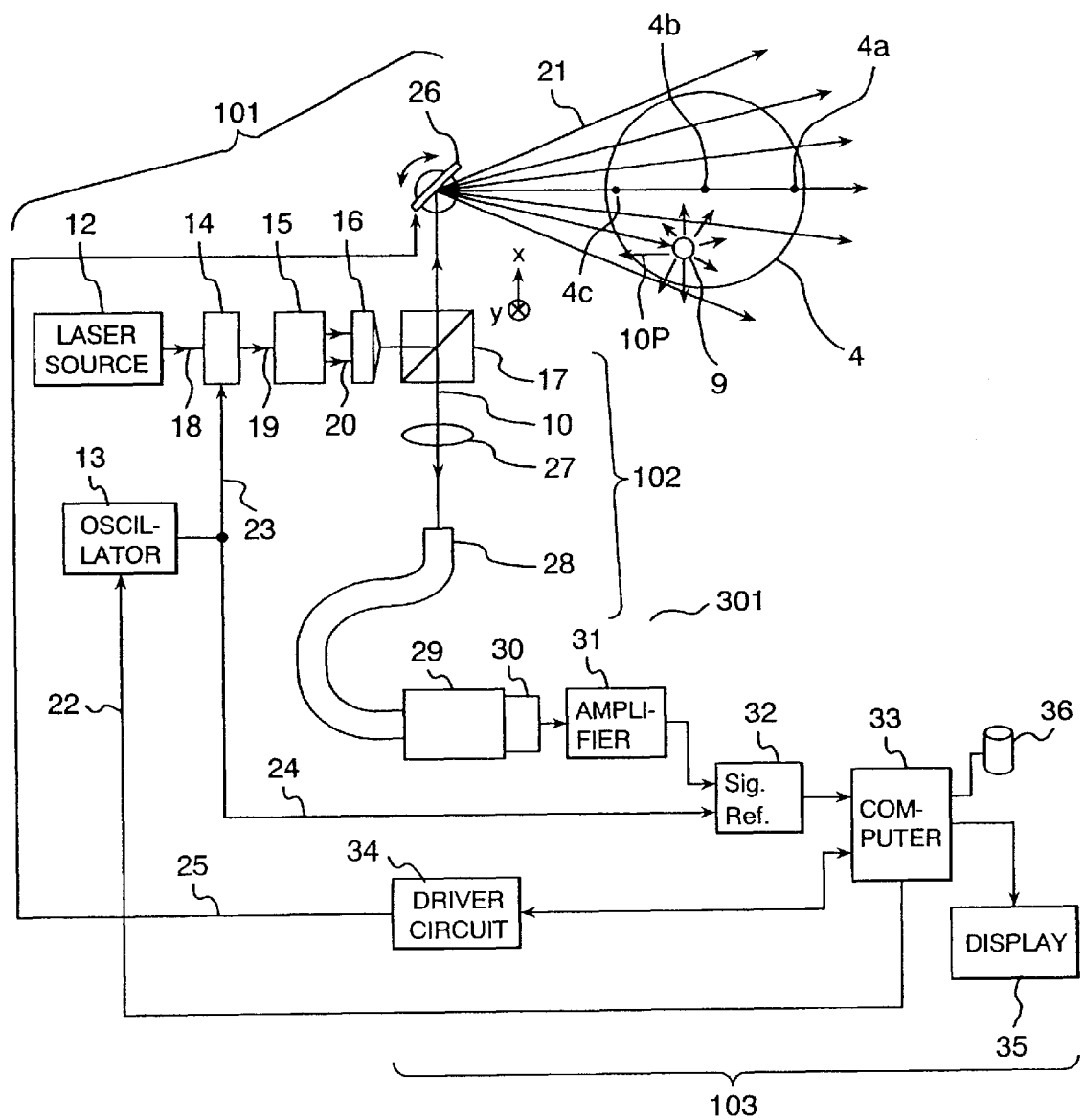
FIG. 2 is a diagram showing a top view of a first embodiment and a material to be processed by the apparatus shown in FIG. 1.

FIG. 2 is a diagram showing a top view of the optical system shown in FIG. 1. The diffractionless beam 21 formed by the axicon 16 is reflected by a polarization beam splitter 17 and then reflected again by a galvano mirror (light scanning means) 26 which is driven at a high speed. The reflected beam then passes through an observation window 11, entering the plasma processing chamber 1. In the plasma processing chamber 1, the beam scans the entire upper surface of the substrate 4. By using the diffractionless beam 21 with a very large depth of focus of 300 mm in this way, it is possible to scan the entire upper surface of the substrate 4 at a uniform energy density, and the scanning at a uniform energy density is one of prominent characteristics of the present invention.

If the diffractionless beam 21 used for scanning at the uniform energy density is further radiated to a floating foreign particle 9 in the plasma 8 or in an area in proximity to the plasma, the beam 21 will be scattered by the floating foreign particle 9. One of lights 10P scattered by the floating foreign particle 9 propagates in the backward-direction along the same optical axis as the incident diffractionless beam 21. This back-scattered light is reflected by the galvano mirror (light scanning means) 26 and a P-polarization component 10 of the reflected light passes through the polarization beam splitter 17 before being converged by an image-formation lens 27 at the entrance-end surface of an optical fiber 28. Since lights reflected directly by portions of the optical system such as a wall surface 1W of the plasma processing chamber 1 and the observation window 11 are each an S-polarization light as is the case with the incident beam 21, they are reflected by the polarization beam splitter 17 and thus do not enter the optical fiber 28. In this way, it is possible to get rid of the lights reflected directly by portions of the optical system such as the wall surface 1W of the plasma processing chamber 1 and the observation window 11.

Figure 7:
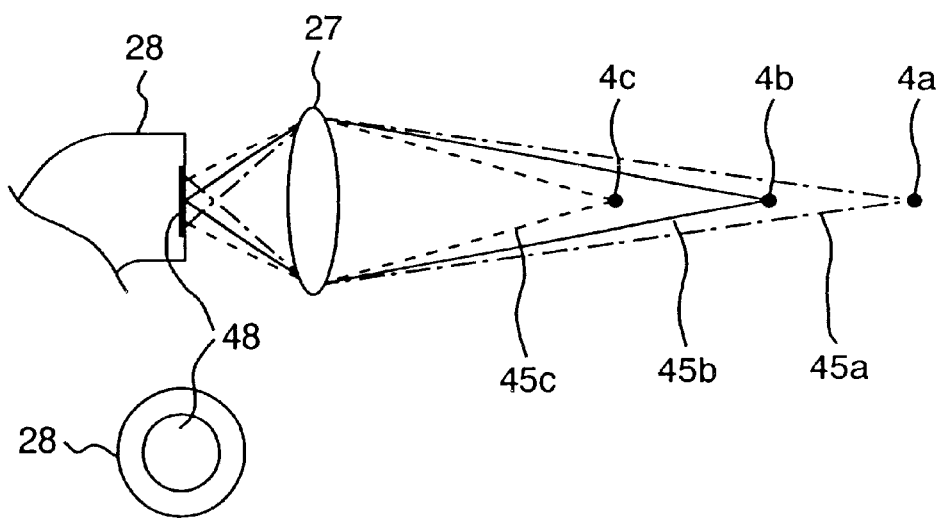
FIG. 7 is a diagram showing reception of the light scattered by foreign particle by using an optical fiber.

As shown in FIG. 7, the center 4b of the substrate 4 and the entrance-end surface of the optical fiber 28 are conjugate each other, that is to say, the center 4b is imaged on the entrance-end surface of the optical fiber 28. A fiber-bundle area (light receiving area) 48 of the entrance-end surface has a size large enough for detecting also scattered lights coming from the ends 4a and 4c separated away from the focus. As a result, through the use of things in conjunction with the diffractionless beam 21, it is possible to scan the entire surface of the substrate 4 at a uniform radiation of energy and a uniform sensitivity. The exit end of the optical fiber 28 is connected to a monochrometer 29 for extracting the same wavelength components as the laser beam 18, that is, components having wavelengths of 532 nm, or 633 nm, or 514.5 nm or 780 nm, or another wavelength in accordance with the laser. The extracted wavelength components are then subjected to photoelectric conversion carried out by a photomultiplier 30. It should be noted that, in place of the monochrometer 29, an interference filter can also be used for the separation of the wavelength components. The detected signal is then amplified by an amplifier 31 employed in the signal processing control system 103. The amplifier 31 has a band width of about 500 kHz which is sufficiently wider than the laser modulation frequency. The amplified signal is then supplied to a synchronous detection circuit 32 which is typically implemented by a lock-in amplifier. In the synchronous detection circuit 32, a rectangular-waveform signal 24, which is used for intensity modulation of the laser beam, with a desired duty in the range typically 40 to 60% and an intensity-modulation frequency of typically 170 kHz, output by the oscillator 13 is used as a reference signal to extract a light component scattered by the foreign particle with an intensity-modulation frequency of typically 170 kHz from the detected signal, supplying the extracted light component to a computer 33. The computer 33 outputs a scanning control signal 25 to the galvano mirror (light scanning means) 26 by way of a driver 34, scanning the diffractionless beam 21 in an area in proximity to the surface of the substrate 4 in order to detect a signal representing lights scattered by the foreign particle at scanning area from time to time. While displaying the intensity of the signal representing lights scattered by the foreign particle at the scanning area on a display unit 35 as a graph in real-time manner, the computer 33 stores the intensity data of each substrate 4 in an internal memory or a storage apparatus 36 provided externally. It should be noted that the internal memory is shown in none of the figures. As the plasma processing such as an etching process or a CVD process carried out on the substrate 4 is completed, the substrate 4 is conveyed out from the plasma processing chamber 1 and the measurement of floating infinitesimal foreign particle on the order of down to sub-microns for the substrate 4 is also ended.

The computer 33 is also capable of supplying a detected signal representing the floating infinitesimal foreign particle observed at the scanning area and associated with the intensity data stored in the storage apparatus 36 for a particular substrate to be processed 4 to an output means such as the display unit 35.

Figure 9:
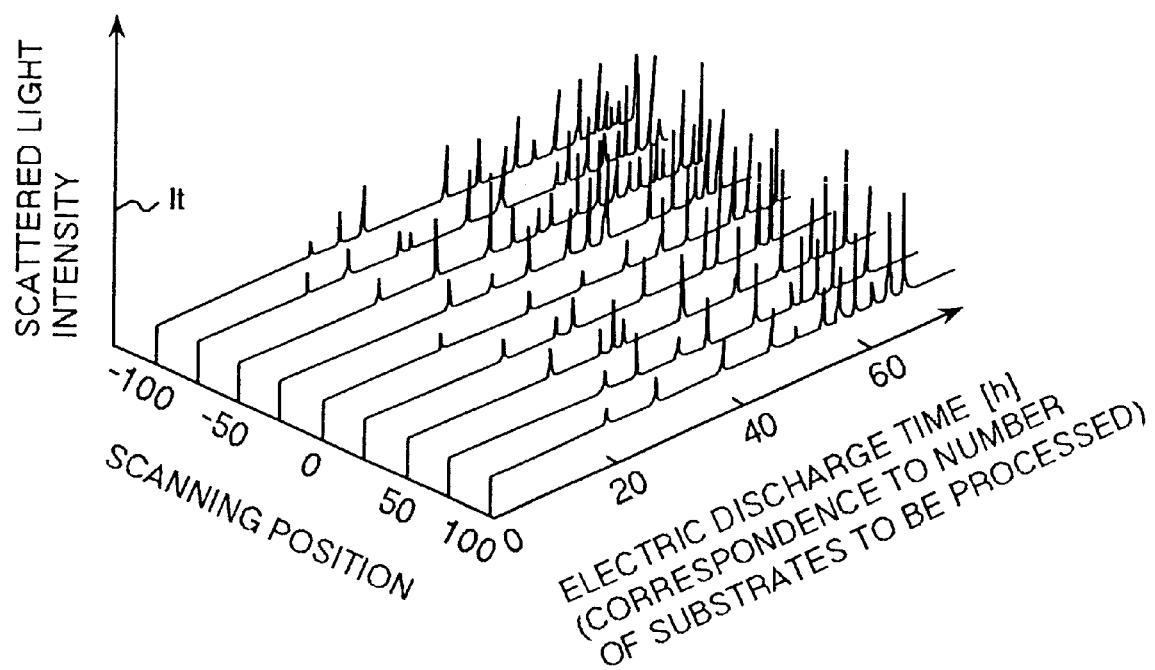
FIG. 9 is a diagram showing variations in the intensity of the scattered from the particle with time at 9 points on a substrate to be processed.

FIG. 9 is a diagram showing variations in intensity of lights scattered by foreign particle with the lapse of cumulative discharge time (h) which represents the number of substrates 4 to be processed each having a diameter of 200 nm. The variations are read out from the storage apparatus 36 to be output to the display unit 35 and displayed thereon. The variations are shown in the figure for each scanning position [mm] on the substrate 4 in the range −100 mm to +100 mm. The scanning positions in the range are selected at intervals of 25 mm. As is obvious from FIG. 9, as the cumulative discharge time (h) lapses, that is, as the number of substrate to be processed 4 increases, the measured number of floating infinitesimal foreign particle also rises.

As described above, by separating weak lights scattered by foreign particle in both the wavelength and frequency domain from a plasma emitted light for a detection purpose, there is exhibited an effect of a substantial increase in sensitivity in the detection of scattered lights even in the case of infinitesimal foreign particle on the order of down to sub-microns floating in a plasma or in an area in proximity to the plasma.

In addition, by using a diffractionless beam, it is possible to scan the entire surface of the substrate at a uniform radiation of energy and a uniform sensitivity, giving rise to an effect of stable detection of foreign particle over the entire surface of the substrate.

Furthermore, the configuration for detection of back-scattered lights by using the scattered-light detecting optical system 102 allows foreign particle floating in a plasma or in an area in proximity to the plasma to be detected with ease in synchronization with a scanning operation carried out by the galvano mirror 26, allowing the laser radiating optical system 101 and the scattered-light detecting optical system 102 to be made compact.

The effects described above allow the state of pollution in the plasma processing chamber to be monitored in a real-time manner and result in another effect of reduction of the number of bad substrates to be processed inadvertently generated due to foreign particle stuck thereto and another effect of an ability to know a time to clean the apparatus with a high degree of accuracy. In addition, the frequency of preventive work to check foreign particle by using a dummy wafer can be reduced to give rise to effects of cost reduction and productivity improvement.

Figure 10:
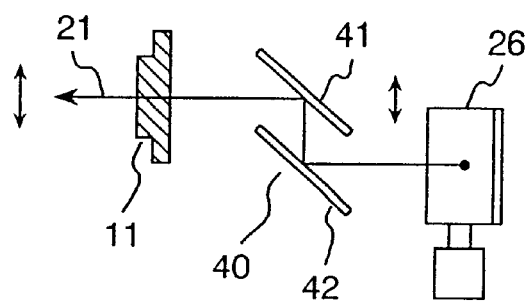
FIG. 10 is a diagram showing an embodiment implementing a height adjusting optical system for adjusting the height of a diffractionless beam relative to a plasma processing chamber.

It should be noted that the position in the height direction relative to the plasma 8 to introduce the diffractionless beam 21 having a spot shape is set in advance at a location where foreign particle float most. The floating-foreign-particle measuring apparatus shown in FIG. 1 is set so that the diffractionless beam 21 is introduced to hit the center of the plasma 8 in the height direction. Normally, however, foreign particles are believed to float most at a lower-side portion of the plasma 8 or at the bulk-sheath boundary portion on the substrate side. It is thus desirable to introduce the diffractionless beam 21 to the lower-side portion of the plasma 8. That is to say, the heights of the laser radiating optical system 101 and the scattered-light detecting optical system 102 are adjusted to a position at which floating foreign particle in the plasma or in an area in proximity to the plasma is most detected. For example, an optical system 40 which can be moved in parallel to the height direction is provided between the observation window 311 and the galvano mirror 26 as shown in FIG. 10. As shown in the figure, the optical system 40 comprises a movable mirror 41 and a fixed mirror 42. By controlling the movement distance of the movable mirror 41, the height of the diffractionless beam 21 with a spot shape can be adjusted.

In addition, by utilizing the rotation of the galvano mirror 26 in conjunction with the movement of the movable mirror 41, the diffractionless beam 21 can be used in a 3-dimensional scanning operation and radiated to the plasma 8. Lights scattered in the backward direction from the plasma 8 are then detected by the scattered-light detecting optical system 102. Then, a component with a wavelength equal to that of the laser beam 18 is extracted by the monochrometer 29 from the detected lights scattered in the backward direction. Subsequently, a light scattered in the backward direction of the extracted component having a wavelength equal to that of the laser beam 18 is received by the photo-multiplier 30 and converted into a signal. Then, by carrying out synchronization detection using the synchronous detection detecting circuit 32 on the signal obtained as a result of the conversion at the intensity-modulation frequency of the laser beam, it is possible to detect a signal representing foreign particle floating in a 3-dimensional space in the plasma or in an area in proximity to the plasma.

It is necessary to further devise a way to prevent materials such as a generated substance produced by the plasma processing from being stuck and deposited to the inner surface of the observation window 11. For example, a protruding shield 38a with an angular cylindrical shape is provided so as to prevent as much as possible reaction generated material from intruding into the inner surface of the observation window 11. By providing such a shield 38a, material such as a generated substance can be prevented from being stuck to the inner surface. In the y-axis direction, it is necessary to adjust the gap between the shields 38a facing each other so as to prevent a side robe 21t surrounding the central spot 21s from being trapped. In the x-axis direction, on the other hand, it is necessary to widen the gap between the shields 38a facing each other so as to prevent the side robe 21t surrounding the central spot 21s from being trapped and to make a scanning operation carried out by the galvano mirror 26 possible. In addition, it is necessary to widen the gap gradually so that, the further we go to the inner side, the wider the gap. Moreover, by providing an exhaust opening for exhausting a generated substance to zones in proximity to the external side of the shield 38a, it is possible to further prevent materials such as a generated substance from being stuck to the inner surface of the observation window 11 for introducing the diffractionless beam 21. In addition, by flowing gas having no effect on the plasma processing from one of shields 38a facing each other to the other, it is possible to further prevent materials such as a generated substance from being stuck to the inner surface of the observation window 11 for introducing the diffractionless beam 21. Examples of the gas having no effect on the plasma processing are inert gas and processing gas. Moreover, by radiating a laser beam for removing materials such as a generated substance stuck to the observation window 11 from the laser radiating optical system 101 at the end of the plasma processing, the inner surface of the observation window 11 can be cleaned. That is to say, it is recommended to have a configuration wherein a laser beam for removing materials such as a generated substance is introduced from a middle of the optical path of the laser radiating optical system 101.

By providing a generated-substance-sticking preventing means for preventing materials such as a generated substance from being stuck to the inner surface of the observation window 11 for introducing the diffractionless beam 21 as described above, it is possible to measure infinitesimal foreign particle on the order of down to sub-microns floating in the plasma or in an area in proximity to the plasma, with a high sensitivity.

Figure 11:
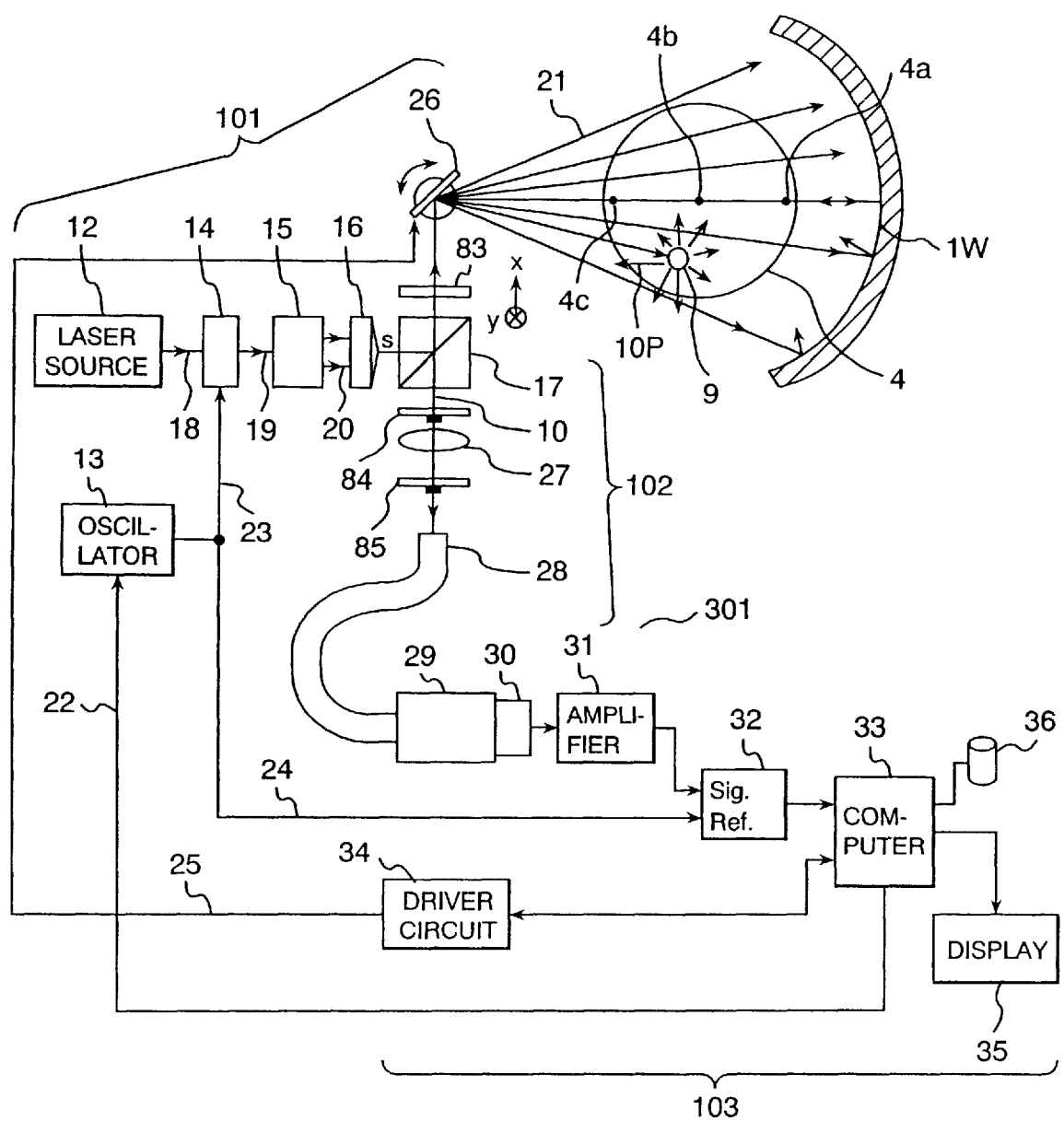
FIG. 11 is a diagram showing a top view of a second embodiment implementing a floating-foreign-particle measuring apparatus employed in a plasma processing apparatus provided by the present invention.

The following is a description of a second embodiment implementing a floating-foreign-particle measuring apparatus 301 provided by the present invention for measuring foreign particle floating in the plasma or in an area in proximity to the plasma with reference to FIG. 11.

The difference between the second embodiment shown in FIG. 11 and the first embodiment described earlier is that the former additionally includes the following:

a λ/4 plate (one-fourth-wavelength plate) 83 provided between the polarization beam splitter 17 and the galvano mirror 26;

a spatial filter 84 having a small disc-like light shielding member at the center thereof provided between the polarization beam splitter 17 and the image-formation lens 27 for shielding a light of a noise component coming from the surface of the observation window 11 on the specular reflection side; and a spatial filter 85 which has a small disc-like light shielding member at the center thereof for shielding lights reflected and scattered by the inner wall 1W of the plasma processing chamber 1 and is placed at a location on which the inner wall 1W is imaged by using the image-formation lens 27. In the configuration described above, an S-polarization laser beam incident to the λ/4 plate 83 is converted into a circular polarization component to be used by the galvano mirror 26 for scanning and radiated to the inside of the plasma processing chamber 1 by way of the observation window 11. The circular polarization component of lights scattered in the backward direction by the floating foreign particle 9 passes through the observation window 11 and is reflected by the galvano mirror 26 before entering the λ/4 plate 83. When passing through the λ/4 plate 83, the lights scattered in the backward direction by the floating foreign particle 9 are all converted into a P-polarization light which then passes through the polarization beam splitter 17 before being converged at the entrance-end surface of the optical fiber 28 by the image-formation lens 27. Thus, the intensity of the lights scattered in the backward direction by the floating foreign particle 9, is increased at the entrance-end surface of the optical fiber 28 and the detection sensitivity of the floating foreign particle 9 are high in comparison with the embodiment shown in FIG. 2. Similarly, the intensities of the specular reflection light from the observation window 11 and the specular reflection light from the side wall 1W inside the plasma processing chamber 1 are also higher. Since the specular reflection light from the observation window 11 is shielded by the spatial filter 84 while the specular reflection light from the side wall 1W inside the plasma processing chamber 1 is shielded by the spatial filter 85 provided at a location in an image-formation relation with the side wall 1W, however, noise components can be eliminated.

As described above, in the embodiment shown in FIG. 11, lights scattered in the backward direction by the floating foreign particle 9 can be detected at a high intensity in comparison with the embodiment shown in FIG. 2. As a result, the detection sensitivity can be increased substantially.

It should be noted that, in the embodiments including that shown in FIG. 2, the surface of the observation window 11, through which the laser beam passes, can be set in an inclined orientation relative to a surface perpendicular to the optical axis so that, by letting the specular reflection light go to a zone outside the visual field of the image-formation lens 27, a noise component if a light reflected from the observation window 11 can be eliminated.

Figure 12:
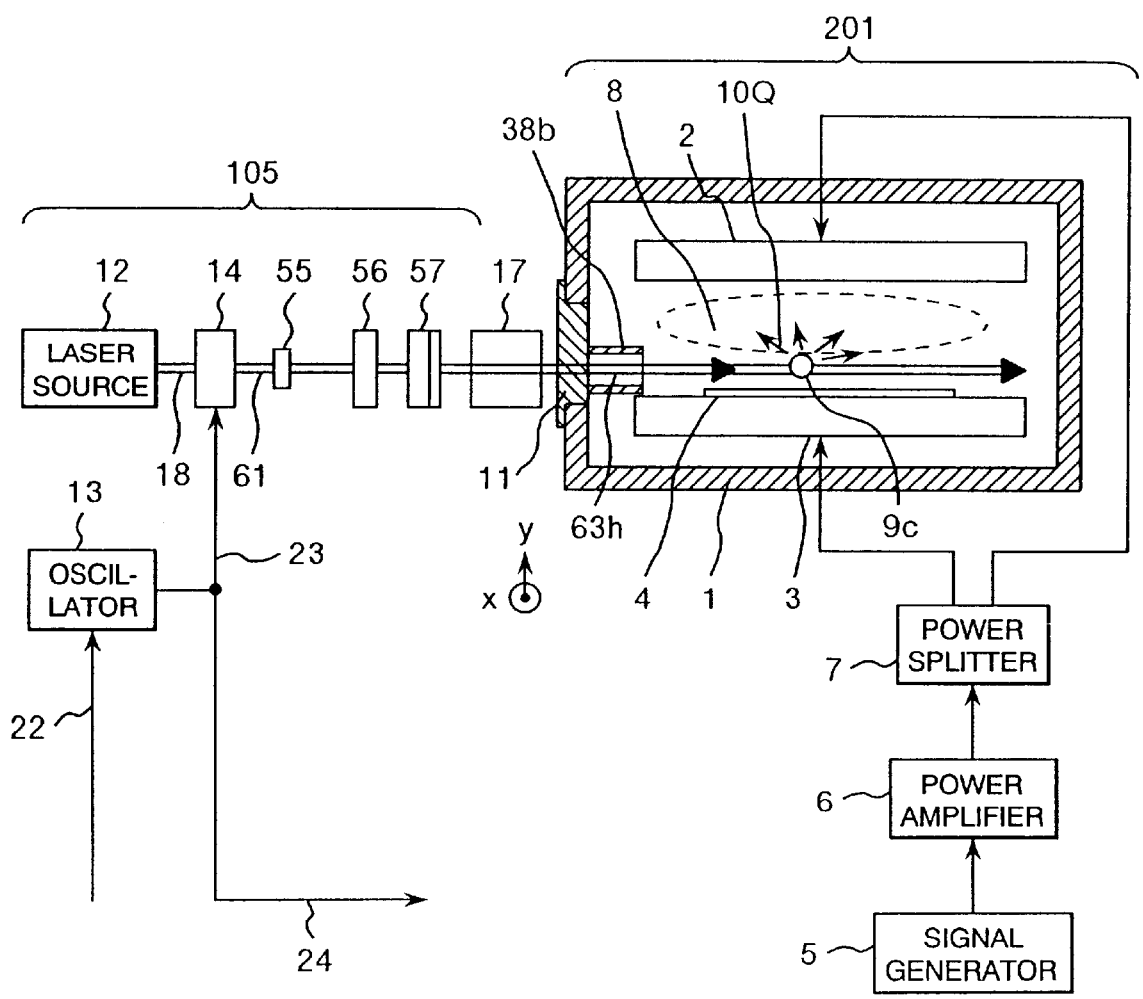
FIG. 12 is a diagram showing a front view of a third embodiment implementing a floating-foreign-particle measuring apparatus employed in a plasma processing apparatus provided by the present invention.
Figure 13:
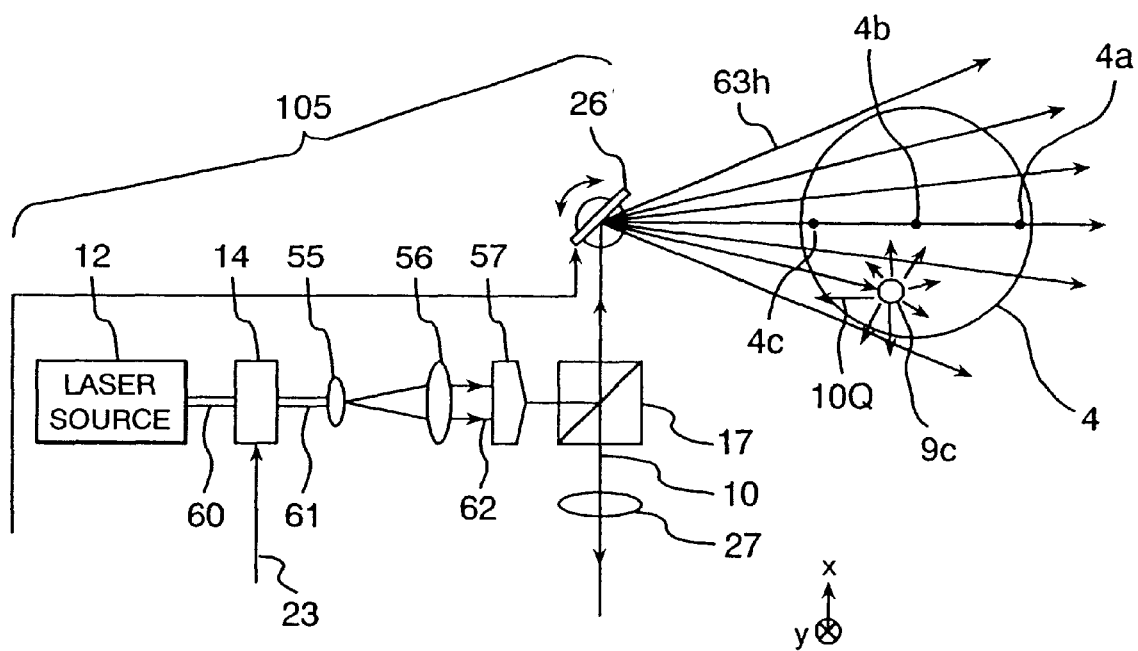
FIG. 13 is a diagram showing a top view of a material to be processed by the apparatus shown in FIG. 12.

The following is a description of a third embodiment implementing the foreign-particle measuring apparatus 301 provided by the present invention for measuring foreign particle floating in the plasma or in an area in proximity to the plasma with reference to FIGS. 12 to 14.

Figure 14A:
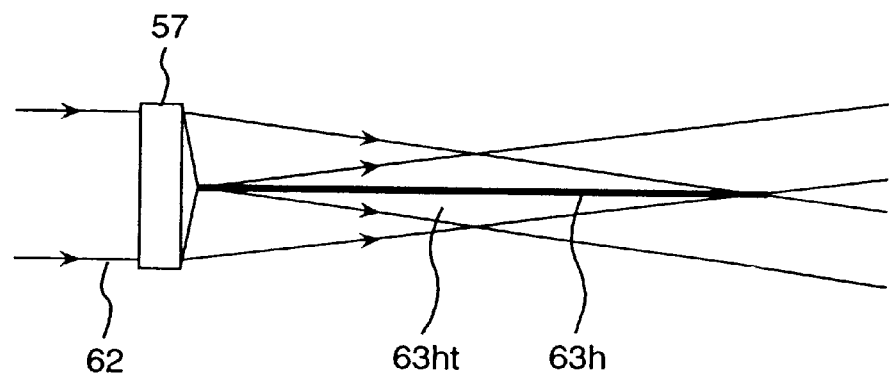
FIG. 14A is a diagram showing a top view of a state of generation of a diffractionless beam on a specific axis by an axicon.
Figure 14B:
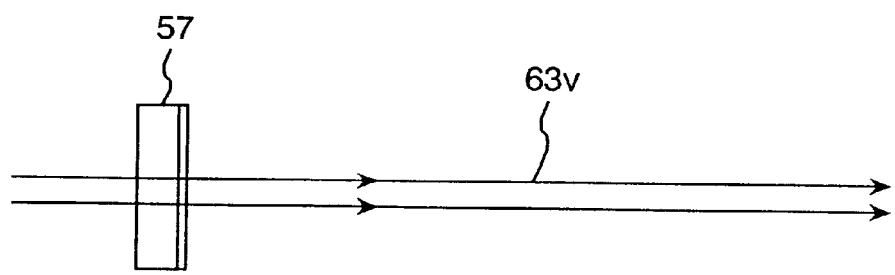
FIG. 14B is a diagram showing a front view of a state of generation of a diffractionless beam on a specific axis by the axicon.
Figure 14C:
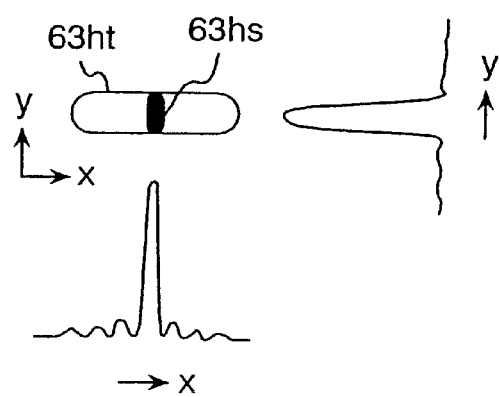
FIG. 14C is a diagram showing an intensity distribution of the diffractionless beam on a 63$h$ surface which is generated by the axicon as showen in FIG. 14A and 14B.

FIG. 12 is a diagram showing a front view of the third embodiment implementing a plasma processing apparatus 201 and a laser radiating optical system 105 of a floating-foreign-particle measuring apparatus. In the third embodiment, the beam expander 15 employed in the laser radiating optical system 101 of the first embodiment shown in FIG. 1 is replaced by a specific-axis (x-axis)-direction beam expander comprising cylindrical lenses 55 and 56 for increasing the beam diameter in the specific-axis (x-axis)-direction as shown in FIGS. 12 and 13. On the other hand, the axicon 16 employed in the laser radiating optical system 101 of the first embodiment shown in FIG. 1 is replaced by a specific-axis (x-axis)-direction axicon 57 also as shown in FIGS. 12 and 13. The rest of the plasma processing apparatus 201, the scattered-light detecting optical system 102 and the signal processing control system 103 have the same configurations and the same functions as the first embodiment, making it unnecessary to repeat their explanation. As shown in FIG. 12, the cylindrical lenses 55 and 56 as well as the axicon 57 are parallel glass plates oriented in the electrode direction or the y-axis direction of the processing chamber 1. Thus, an S-polarization beam 61 emitted by the laser source 12 and then subjected to intensity modulation in the intensity modulator 14 passes through the cylindrical lenses 55 and 56 as well as the specific-axis (x-axis)-direction axicon 57 oriented in the electrode direction or the y-axis direction as a beam 63V with a diameter in the range abort 0.5 to 3 mm which is equal to that in the laser emanating state as shown in FIG. 14B. In the direction perpendicular to the electrode or the x-axis direction, that is, in the surface direction of the substrate 4, on the other hand, the cylindrical lenses 55 and 56 are each a convex lens while the specific-axis (x-axis)-direction axicon 57 has a shape with the intrinsic vertex angle as shown in FIG. 13. Thus, after being expanded by the cylindrical lenses 55 and 56, the beam 61 completing the intensity modulation is converted by the specific-axis (x-axis)-direction axicon 57 into a diffractionless beam 63h as shown in FIG. 14A. As a result, a thin long spot 63hs is formed along the optical axis as shown in FIG. 14C. The spot 63hs has a height in the range about 0.5 to 3 mm in the electrode direction or the y-axis direction and a width in the range about 10 to 30 μm in the surface direction of the substrate 4 or the x-axis direction. Much like the first embodiment, the diffractionless beam 63h is reflected by the polarization beam splitter 17 and then reflected by the galvano mirror 26 which is driven at a high speed. Subsequently, the diffractionless beam 63h enters the plasma processing chamber 1 by way of the observation window 11, and the beam 63h is scanned in an area in proximity to the entire surface of the substrate 4. As shown in FIG. 12, in general, floating foreign particle 9c in the plasma 8 is trapped on a bulk-sheath boundary surface right above the substrate 4 and said to exist in a polarized state in this area. It is an object of the third embodiment to detect the foreign particle 9c trapped on a bulk-sheath boundary surface. In the case of the first embodiment, if the diffractionless beam 21 shown in FIG. 6B is scanned in an area in proximity to a surface of the substrate 4, the side robe 21t surrounding the central spot 21s is distorted by the substrate 4, causing a condition for generating a diffractionless beam to collapse. As a result, the central spot 21s is not formed any more. In the case of the third embodiment, on the other hand, a side robe 63ht is formed in the surface direction of the substrate 4 as shown in FIG. 14C. Thus, the diffractionless beam 63h can be scanned in an area in proximity to the surface of the substrate 4 by letting the beam 63h approach an area as close as possible to the substrate 4. As a result, it is possible to detect the foreign particle 9c trapped on a bulk-sheath boundary surface.

In addition, it is necessary to devise a way to prevent materials such as a generated substance produced by the plasma processing from being stuck and deposited to the inner surface of the observation window 11. For example, a protruding shield 38b with an angular cylindrical shape is provided so as to prevent as much as possible a reaction generated material from intruding into the inner surface of the observation window 11. In the y-axis direction, the gap between the shields 38b facing each other can be narrowed to a value corresponding to a diameter in the range about 0.5 to 3 mm, a diameter equal to that in the laser emanation state, so as to much prevent a deposited material from being stuck to the inner surface of the observation window 11. In the x-axis direction, on the other hand, it is necessary to widen the gap between the shields 38b facing each other so as to prevent the side robe 63ht surrounding the central spot 21hs from being trapped and to make a scanning operation carried out by the galvano mirror 26 possible. In addition, it is necessary to widen the gap gradually so that, the further we go to the inner side, the wider the gap. Moreover, by providing an exhaust opening for exhausting a reaction generated substrate to zones in proximity to the external side of the shield 38b, it is possible to further prevent materials such as a generated substance from being stuck to the inner surface of the observation window 11 for introducing the diffractionless beam 63h. In addition, by flowing gas having no effect on the plasma processing from one of shields 38b facing each other to the other, it is possible to further prevent materials such as a generated substance from being stuck to the inner surface of the observation window 11 for introducing the diffractionless beam 21. Examples of the gas having no effect on the plasma processing are inert gas and processing gas.

As described above, by preventing materials such as a generated substance from being stuck to the inner surface of the observation window 11 for introducing the diffractionless beam 21, it is possible to measure foreign particle on the order of down to sub-microns floating in the plasma or in an area in proximity to the plasma at a high sensitivity.

It should be noted that, also in the third embodiment, it is necessary to set the height of the incident diffractionless beam 63h relative to the substrate 4 so that the high sensitivity can be obtained.

As described above, according to the third embodiment, not only are the same effects as the first embodiment obtained, but a foreign particle trapped on the plasma bulk-sheath boundary surface can also be detected. As a result, there are exhibited effects that the sensitivity to detect a foreign particle is increased substantially and the state of pollution in the plasma processing chamber of the etching apparatus can be controlled with a high degree of precision.

Figure 15:
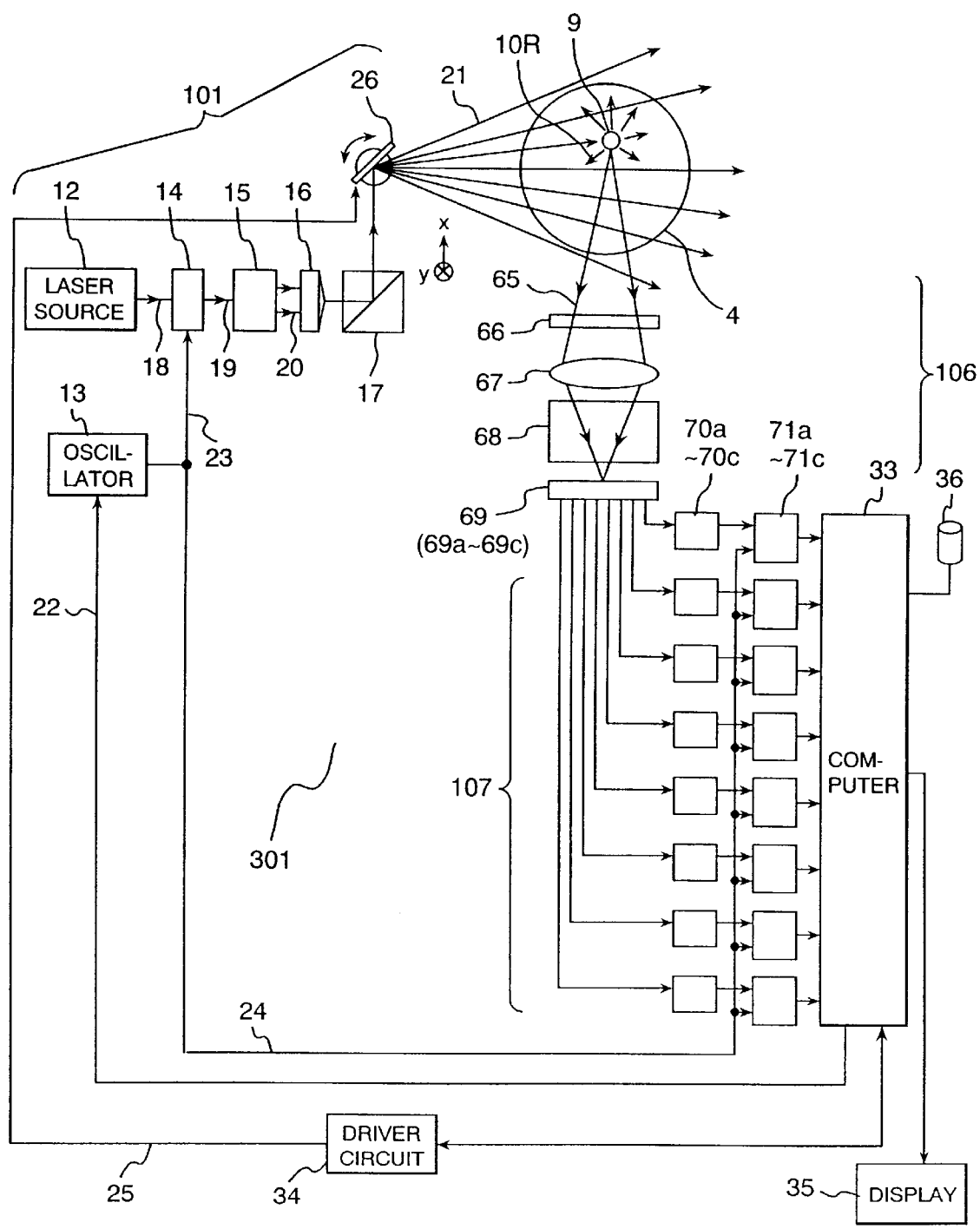
FIG. 15 is a diagram showing a top view of a fourth embodiment implementing a floating-foreign-particle measuring apparatus employed in a plasma processing apparatus provided by the present invention.
Figure 16:
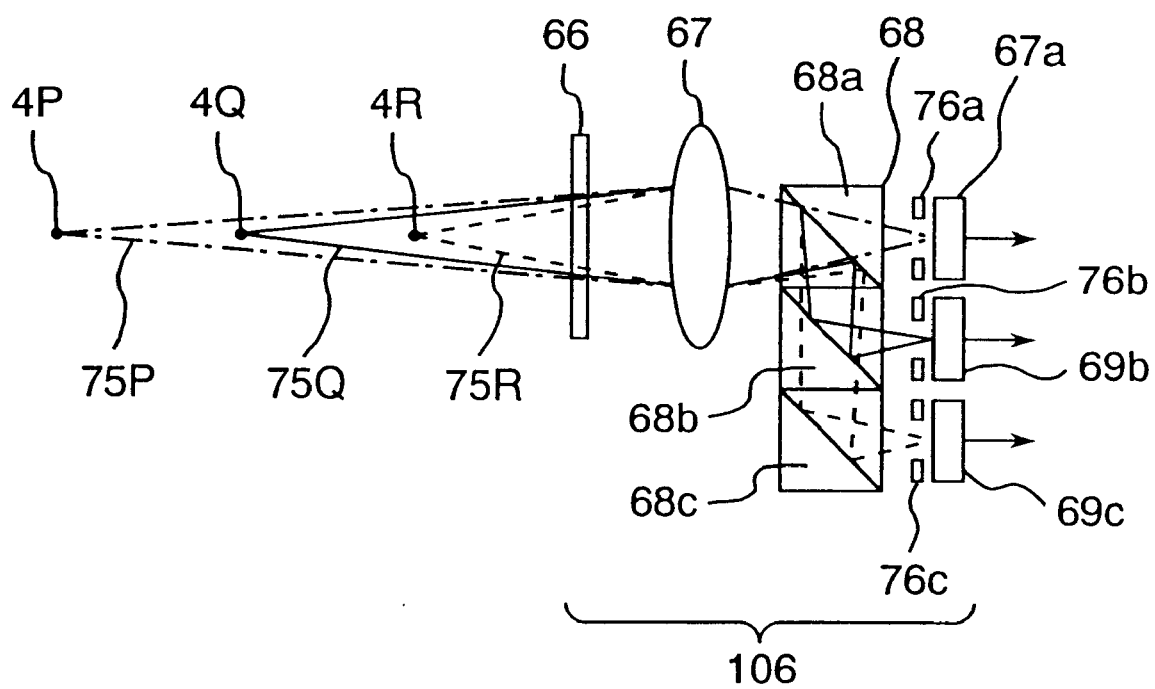
FIG. 16 is a diagram showing a side view of a scattered-light detecting optical system shown in FIG. 15.

Next, a fourth embodiment implementing the foreign-material measuring apparatus 301 provided by the present invention for measuring foreign particle floating in the plasma or in an area in proximity to the plasma is explained by referring to FIGS. 15 and 16.

FIG. 15 is a diagram showing a top view of a fourth embodiment implementing a floating-foreign-particle measuring apparatus as seen from a position above a substrate to be processed. As shown in the figure, the floating-foreign-particle measuring apparatus comprises a laser radiating optical system 101, a scattered-light detecting optical system 106 and a signal processing control system 107. Since the laser radiating optical system 101 has the same configuration and functions as the first embodiment, it is not necessary to repeat the explanation thereof. The fourth embodiment is much different from the first to third embodiments in that the latter detects back-scattered lights from a foreign particle while the former has a configuration wherein it is side-direction scattered lights that are detected. As shown in FIG. 15, side-direction scattered lights 65 of all scattered lights 10R coming from a foreign particle 9 hit an interference filter 66 employed in the scattered-light detecting optical system 106. The interference filter 66 separates wavelength components having typical wavelengths of 532 nm, or 633 nm, or 514.5 nm or 780 nm equal to those of the laser beam 21. The separated wavelength components are converged by an image-formation lens 67, being focused on photo-diode arrays 69a, 69b and 69c each having an 8-channel parallel output type by way of an optical-path-length correcting prism 68. FIG. 16 is a diagram showing a side view of the scattered-light detecting optical system 106. As shown in FIG. 16, the optical-path-length correcting prism 68 comprises 3 units 68a, 68b and 68c. The optical-path-length correcting prism 68 corrects the lengths of the optical paths of scattered lights coming from points 4P, 4Q and 4R along the optical axis on the substrate 4 and from locations in proximity to the points 4P, 4Q and 4R. As a result, the scattered lights form an image on the 3 photo-diode arrays 69a, 69b and 69c after passing through pin holes 76a, 76b and 76c respectively. The 3 photo-diode arrays 69a, 69b and 69c supply a 24 (=3×8)-channel output signal to the signal processing control system 107 wherein the output signal is amplified by 8-channel amplifiers 70a, 70b and 70c. The amplified signal is then supplied to 8-channel synchronous detection units 71a, 71b and 71c. In the synchronous detection units 71a, 71b and 71c, a rectangular-waveform signal 24 with a desired duty of typically 50% and an intensity-modulation frequency of typically 170 kHz, output by an oscillator 13 is used as a reference signal for synchronization detection. It should be noted that the rectangular-waveform signal 24 is also used for intensity modulation of the laser beam. As a result of the synchronization detection, a foreignparticle-scattered-light component with a typical intensity-modulation frequency of 170 kHz is extracted from the 24-channel detected signal and supplied to a computer 33. The computer 33 outputs a scanning control signal 25 to the galvano mirror (light scanning means) 26 by way of a driver 34, scanning the diffractionless beam 21 in an area in proximity to the surface of the substrate 4 in order to detect a signal representing lights scattered by the foreign particle at scanning area from time to time. The computer 33 stores the intensity data of each substrate 4 in an internal memory or a storage apparatus 36 provided externally. It should be noted that the internal memory is shown in none of the figures. As the plasma processing such as an etching process or a CVD process carried out on the substrate 4 is completed, the substrate 4 is conveyed out from the plasma processing chamber 1 and the measurement of the floating foreign particles for the substrate 4 is also ended.

The computer 33 is also capable of supplying a detected signal representing the floating foreign particle observed at the scanning area and associated with the intensity data stored in the storage apparatus 36 for a particular substrate to be processed 4 to an output means such as the display unit 35.

In particular, in the case of the fourth embodiment, it is necessary to provide an incident-light window 11 used for introducing the diffractionless beam 21 into the plasma processing chamber 1 and an observation window with a rectangular shape. Shown in none of the figures, the observation window has an area large enough for exhausting weak side-direction scattered lights out from the plasma processing chamber 1. It is thus necessary to all but completely prevent materials such as a generated substance from being stuck and deposited to the inner surface of the observation window having a large area to say nothing of the incident-light window 11.

By configuring the incident-light window 11 in the same way as the first and second embodiments described earlier, it is possible to prevent materials such a generated substance from being stuck and deposited to the inner surface of the incident-light window 11. As for the observation window with a rectangular shape having a large area, upper and lower protrusions facing each other are provided on the inner side. By flowing gas having no effect on the plasma processing from one of the protrusions to the other, it is possible to further prevent materials such as a generated substance from being stuck and deposited to the inner surface of the observation window. Examples of the gas having no effect on the plasma processing are inert gas and processing gas.

Nevertheless, the necessity to completely prevent materials such as a generated substance from being stuck and deposited to the inner surface of the observation window with a rectangular shape having a large area is a problem that remains to be solved.

Not only does the fourth embodiment provide the same effects as the first embodiment, but the negative effect of reflected light coming from the inner wall of the plasma processing chamber 1 can also be reduced by detecting side-direction scattered lights. As a result, the fourth embodiment also provides an effect of a substantially increased sensitivity of detection of a foreign particle. As described above, however, the fourth embodiment has a problem that it is absolutely necessary to prevent materials such as a generated substance from being stuck and deposited to the inner surface of the observation window with a rectangular shape having a large area.

In addition, it is also possible to install the scattered-light detecting optical system 106 at a location facing the galvano mirror 26 so as to construct a configuration for detecting forward-direction scattered lights. In this case, it is necessary to provide a light shielding plate or a polarization plate for shielding a directly incident S-polarization diffractionless beam.

Figure 17:
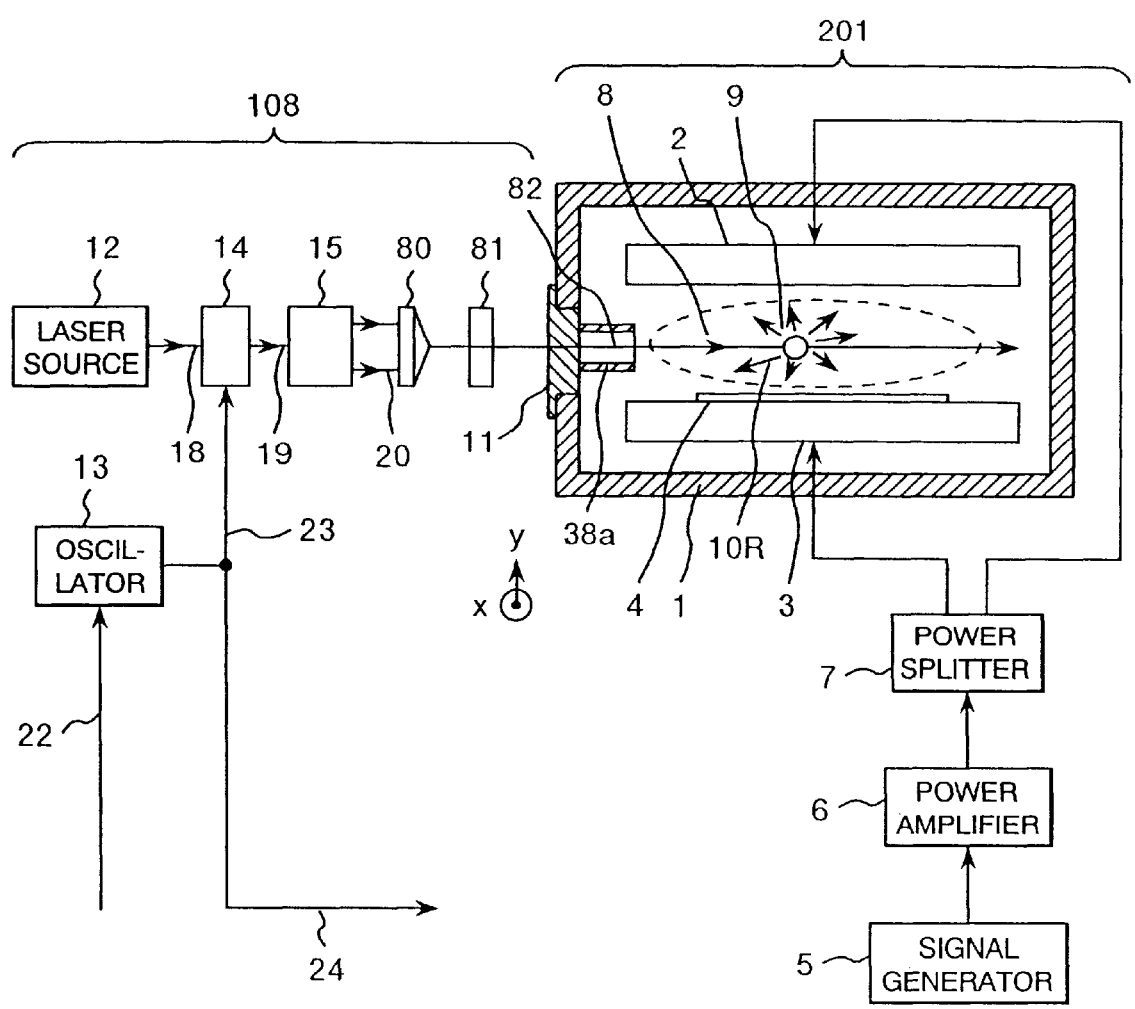
FIG. 17 is a diagram showing a front view of a fifth embodiment implementing a floating-foreign-particle measuring apparatus employed in a plasma processing apparatus provided by the present invention.
Figure 18:
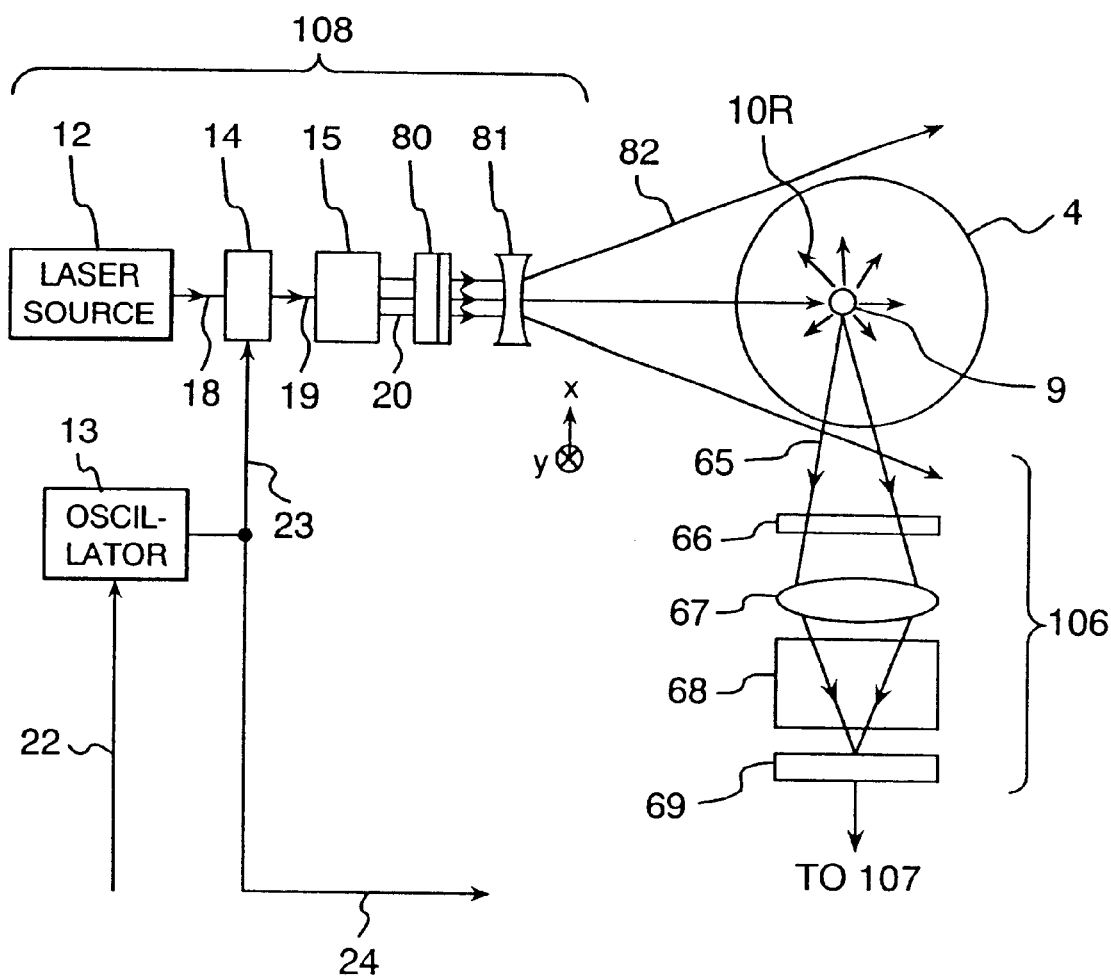
FIG. 18 is a diagram showing a top view of FIG. 17.

The following is a description of a fifth embodiment implementing the floating-foreign-particle measuring apparatus 301 for measuring a foreign particle floating in the plasma or in an area in proximity to the plasma with reference to FIGS. 17 and 18.

FIG. 17 is a diagram showing a front view of the fifth embodiment implementing the floating-foreign-particle measuring apparatus and the plasma processing apparatus 201 whereas FIG. 18 is a diagram showing a top view thereof as seen from a position above the substrate. The plasma-floating-foreign-material measuring apparatus comprises the laser radiating optical system 108 shown in FIG. 17, the scattered-light detecting optical system 106 shown in FIG. 18 and the signal processing control unit 107 (not shown in figures). As shown in FIG. 17, in the laser radiating optical system 108, an S-polarization beam 18 emanating from a laser source 12 is subjected to intensity modulation carried out by an intensity modulator 14 which is typically implemented by an AO modulator. A beam 19 completing the intensity modulation is then expanded by the beam expander 15. An expanded beam 20 then enters a specific-axis (y-axis) axicon 80. The specific-axis (y-axis) axicon 80 has a shape with the intrinsic vertex angle in the electrode direction or the y-axis direction. In a direction perpendicular to the electrode or the x-axis direction, that is, in the surface direction of the substrate, on the other hand, the specific-axis axicon 80 has a shape of a glass plate as shown in FIG. 18. Thus, after passing through the axicon 80, the beam turns into a diffractionless beam having a width in the range about 15 to 30 $\mu$m in the electrode direction or the y-axis direction. In the surface direction of the substrate 4 or the x-axis direction, on the other hand, the beam remains as an expanded beam as it is. As shown in FIGS. 17 and 18, this beam is converted by a cylindrical concave lens 81 into a beam 82 spreading to form a fan-like shape in the surface direction of the substrate 4. That is to say, unlike the first to fourth embodiments, in the case of the fifth embodiment, the beam scanning operation carried out by the galvano mirror 26 is no longer required. Side-direction scattered lights 65 of all scattered lights 10R coming from foreign particle 9 are detected by the scattered-light detecting optical system 106. Since the scattered-light detecting optical system 106 and the signal processing control unit 107 have the same configurations and functions as those of the fourth embodiment, it is not necessary to repeat their explanations.

According to the fifth embodiment, not only are the same effects as the first embodiment obtained, but there is also exhibited an effect that the apparatus configuration becomes simple and compact because the beam scanning system is not required. In order to measure infinitesimal floating foreign particle on the order of down to sub-microns, however, it is necessary to intensify lights scattered from the infinitesimal floating foreign particle. It is thus necessary to increase the intensity of the beam 82 spreading to form a fan shape in the surface direction of the substrate to the same level as the scanning operation carried out by using the galvano mirror 26. It is therefore necessary to employ a light source that is capable of generating a laser beam with a high intensity as the laser source 12. In this case, it is possible to employ a laser source 12 capable of outputting an S-polarization pulse laser which has a high intensity and oscillates at a frequency different from the plasma excitation frequency. In addition, by including the function of the oscillator 13 in the laser source, the intensity modulator 14 becomes unnecessary.

It should be noted that, much like the fourth embodiment, it is also possible to install the scattered-light detecting optical system 106 at a location facing the cylindrical concave lens 81 so as to construct a configuration for detecting forward-direction scattered lights. In this case, it is necessary to provide a light shielding plate or a polarization plate for shielding a directly incident S-polarization diffractionless beam.

In addition, much like the first to third embodiments, by detecting the back-scattered lights, only one observation window 11 is needed and it is possible to narrow the area of the observation window 11 to such an extremely small value that materials such as a generated substance is not stuck and deposited on the area. Thus, a measure for preventing materials such as a generated substance from being stuck to the observation window 11 can be implemented with ease and a high degree of reliability as described before. As a result, it also becomes possible to measure infinitesimal foreign particle on the order of down to sub-microns floating in the plasma or in an area in proximity to the plasma with a high degree of sensitivity. It should be noted that, since forward-direction scattered lights are detected, it is also possible to optically eliminate lights directly reflected by the inner wall 1W of the plasma processing chamber 1 and the observation window 11 as well as scattered lights reflected from the inner wall 1W with ease as described earlier. In addition, the laser radiating systems 101, 104 and 105 as well as the scattered-light detecting optical system 102 can be made compact.

Furthermore, by feeding back a result of measurement of a foreign particle floating in the plasma or in an area in proximity to the plasma to means for reducing the quantity of a generated substance stuck to the inner wall of the plasma processing chamber and the side wall of the electrode and by controlling the means on the basis of the fed-back result, it is possible to reduce the quantity of a generated substance stuck to the inner wall of the plasma processing chamber and the side wall of the electrode. It should be noted that the means typically include a means for controlling the temperature of the inner wall of the plasma processing chamber and the side wall of the electrode in addition to a means for generating a magnetic field over the inner wall of the plasma processing chamber.

Figure 19:
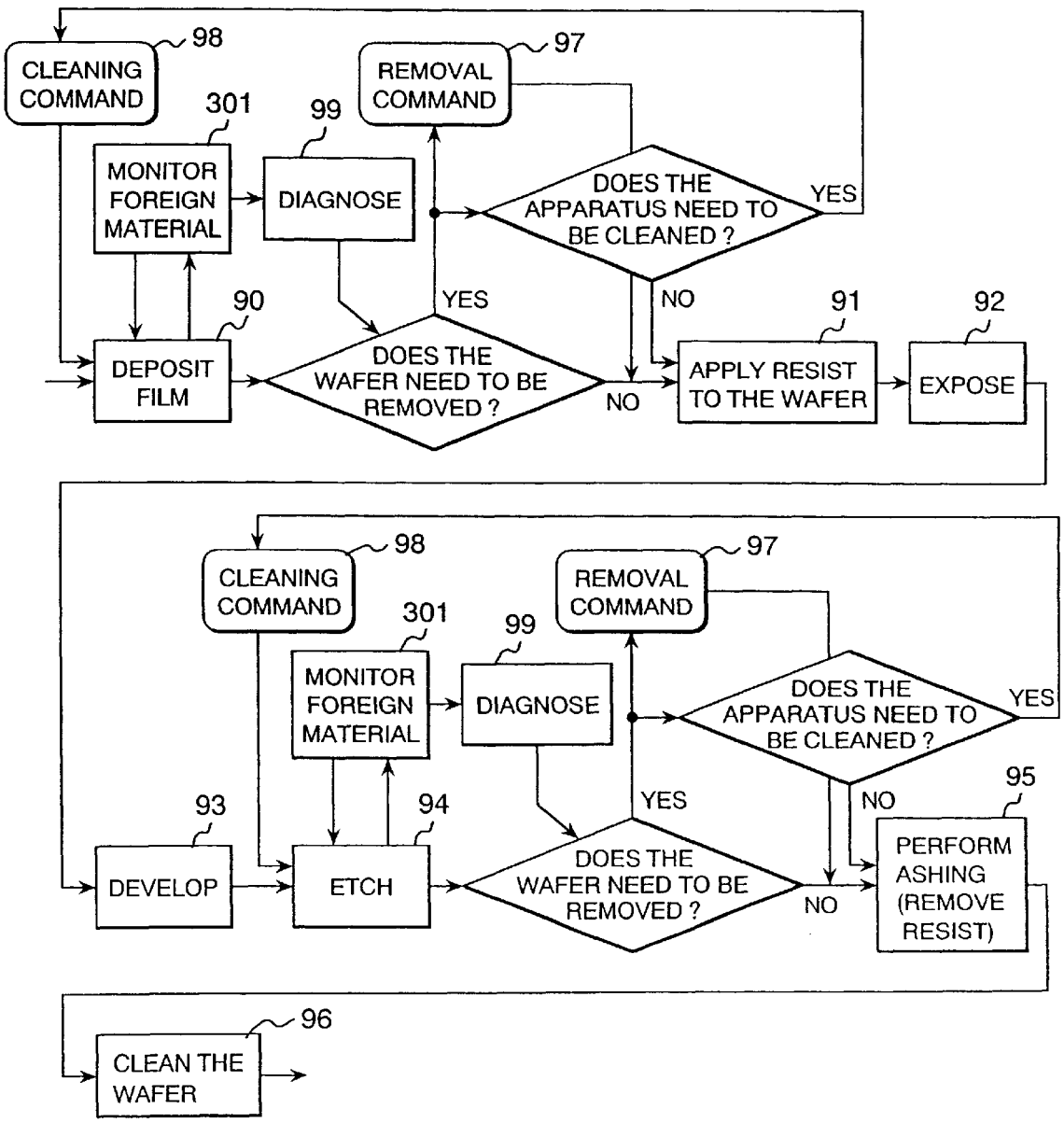
FIG. 19 is a diagram showing an embodiment implementing a photolithography process of a semiconductor manufacturing line carried out by various kinds of plasma processing apparatus employing a floating-foreign-particle measuring apparatus provided by the present invention.
Figure 20:
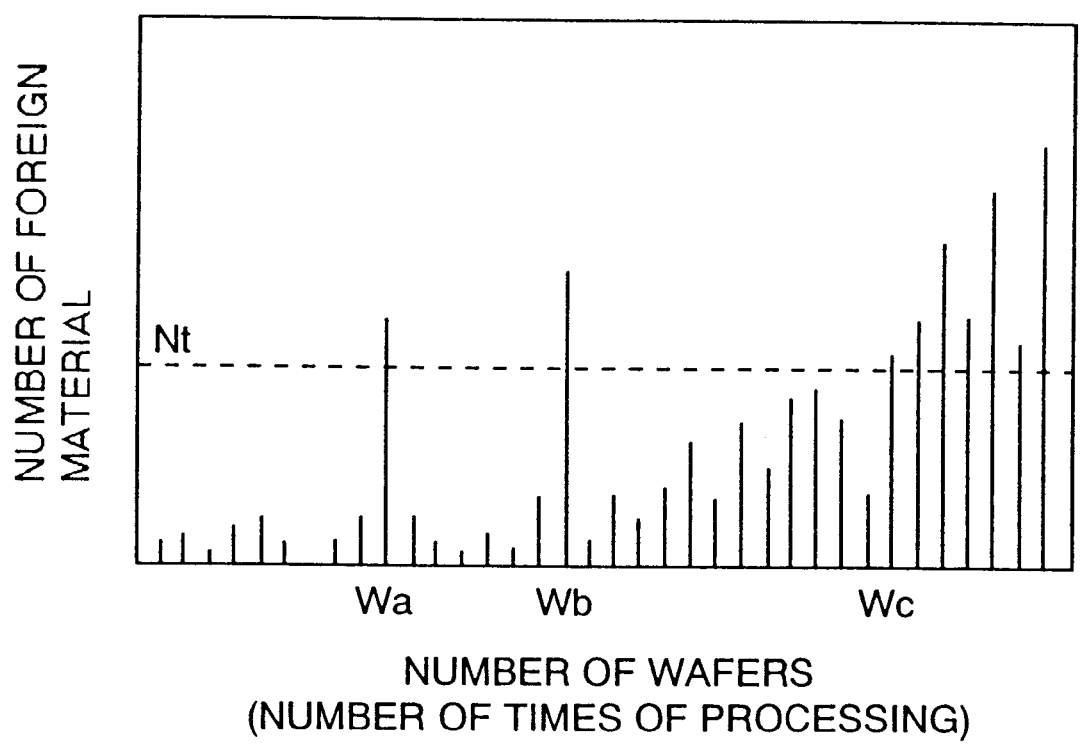
FIG. 20 is a diagram showing variations in the number of foreign particles with the number of wafers.

The following is a description of an embodiment implementing a semiconductor manufacturing line for manufacturing semiconductor devices including semiconductor substrates such as semiconductor wafers by using the plasma processing apparatuses 201 (or, to be more specific, 90 and 94) each provided with the floating-foreign-particle measuring apparatus 301 for measuring foreign particle floating in a plasma or in an area in proximity to the plasma, provided by the present invention with reference to FIGS. 19 and 20.

In this embodiment, one of the plasma processing apparatuses 201 is a film depositing apparatus 90 and the other is an etching apparatus 94 which operate in a photolithography process of the semiconductor manufacturing line. As described above, the film depositing apparatus 90 and the etching apparatus 94 are each provided with the floating-foreign-particle measuring apparatus 301 for implementing control of foreign particle on a semiconductor wafer and foreign particle in each apparatus.

First of all, the film depositing apparatus 90 (201) forms a film to be manufactured such as a film made of silicon oxide on the semiconductor wafer. In the course of film formation, the floating-foreign-particle measuring apparatus 301 measures the number of foreign particle floating in the plasma or in an area in proximity to the plasma for each substrate to be processed (semiconductor wafer), and a diagnosing unit 99 diagnoses the total number of such foreign particles at the end of the film formation. The diagnosing unit 99 can be implemented by the computer 33 employed in the signal processing control system 103 or 107, or by a CPU other than the computer 33. When the total foreign-particle count for a substrate to be processed (a semiconductor wafer) exceeds a threshold value Nt as shown in FIG. 20, for example, the diagnosing unit 99 issues a command to remove the substrate from the semiconductor manufacturing line. In the example shown in FIG. 20, the substrates to be removed are semiconductor wafers Wa and Wb. As a result, the semiconductor wafers Wa and Wb are removed from the semiconductor manufacturing line and not conveyed by a conveying means (not shown in figures) to a next process such as a resist applying process. In addition, when the total foreign-particle count exceeds the threshold value Nt for a plurality of consecutive substrates to be processed following a semiconductor wafer Wc, the diagnosing unit 99 issues a command to clean the film depositing apparatus 90. A substrate to be processed or a semiconductor wafer for which the total foreign-particle count is smaller than the threshold value Nt is conveyed to typically a resist applying apparatus 91 by the conveying means (not shown in figures). In the resist applying apparatus 91, the substrate is coated with resist. After the resist applying process, an exposure apparatus 92 transfers a desired circuit pattern formed on a mask or a reticule to the applied resist on the substrate. Pieces of resist corresponding to the transferred circuit pattern are removed by a development apparatus 93 from the substrate or the semiconductor wafer completing the exposure process before the substrate is supplied to the etching apparatus 94 (201).

In the etching apparatus 94 (201), pieces of manufactured film beneath the removed pieces of resist are etched off from the processed wafer. That is to say, a resist pattern remaining on the film serves as a mask. Much like the film depositing apparatus 90, in the course of etching, the floating-foreign-particle measuring apparatus 301 measures the number of foreign particle floating in the plasma or in an area in proximity to the plasma for each substrate to be processed or each semiconductor wafer, and a diagnosing unit 99 diagnoses the total number of such foreign particle at the end of the etching process. The diagnosing unit 99 can be implemented by the computer 33 employed in the signal processing control system 103 or 107, or by a CPU other than the computer 33. When the total foreign-particle count for a substrate to be processed or a semiconductor wafer exceeds the threshold value Nt as shown in FIG. 20, for example, the diagnosing unit 99 issues a command to remove the substrate from the semiconductor manufacturing line. In the example shown in FIG. 20, the substrates to be removed are semiconductor wafers Wa and Wb. As a result, the semiconductor wafers Wa and Wb are removed from the semiconductor manufacturing line and not conveyed by a conveying means (not shown in figures) to a next process such as an ashing process. In addition, when the total foreign-particle count exceeds the threshold value Nt for a plurality of consecutive substrates to be processed following a semiconductor wafer Wc, the diagnosing unit 99 issues a command to clean the etching apparatus 94. In response to such a cleaning command, the operation to supply a substrate to be processed or a semiconductor wafer to the etching apparatus 94 is terminated and the etching apparatus 94 is cleaned. A substrate to be processed or a semiconductor wafer for which the total foreign-particle count is smaller than the threshold value Nt is conveyed to typically an ashing apparatus 95. In the ashing apparatus 95, the remaining pieces of resist are removed. The substrate is then supplied to a cleaning apparatus 96 for cleaning the substrate.

According to the present embodiment, a film depositing apparatus and an etching apparatus which operate in a photolithography process are each provided with the floating-foreign-particle measuring apparatus 301 based on the first to fifth embodiments so that it is possible to carry out real-time monitoring of the state of pollution in a processing chamber for each of the film depositing apparatus and the etching apparatus. As a result, there are exhibited an effect that it is possible to fabricate a semiconductor device having a high quality by suppressing generation of bad substrates to be processed or bad semiconductor wafers caused by foreign particle stuck thereto. In addition, there is also exhibited an effect of knowing the time to clean the film depositing apparatus and the etching apparatus with a high degree of accuracy. Moreover, the frequency of preventive work to check foreign particle by using a dummy wafer can be reduced to give rise to effects of cost reduction and productivity improvement. Furthermore, the entire manufacturing line can be automated.

In the embodiments described above, the high frequency of electric power for plasma excitation is set at 400 kHz whereas the intensity-modulation frequency of the laser is set at 170 kHz. It should be noted, however, that the scope of the present invention is not limited to such frequencies. In addition, while the etching apparatus used as a plasma processing apparatus as implemented by the above embodiment is implemented by a plasma etching apparatus of the parallel-plate type, the scope of the present invention is not limited to such an implementation. It is needless to say that the present invention can also be applied to a variety of etching apparatuses such as an ECR etching apparatus and a microwave etching apparatus. Furthermore, in the first to fifth embodiments described above, the present invention is applied to an etching apparatus used as a plasma processing apparatus. It is worth noting, however, that the scope of the present invention is not limited to such an implementation. For example, the present invention can also be well applied to a film forming apparatus such as a plasma CVD apparatus. Moreover, the present invention can also be applied basically to a film forming apparatus not using a plasma such as a sputter-processing apparatus. In addition, the substrate is not limited to a semiconductor wafer. The substrate can be a substrate for liquid-crystal display devices or a semiconductor laser device. Furthermore, the embodiments described above exemplify implementation of separation of frequencies and separation of wavelengths in combination with use of a diffractionless beam. It should be noted, however, that the three do not necessarily have to be implemented simultaneously. Only one or two of them can also be implemented in dependence on the state of disturbances generated by the apparatus in question such as the amount of foreign particles to be detected and the plasma emitted light.

As described above, according to the present invention, by separating weak scattered lights emanating from foreign particle on the order of down to sub-microns floating in a plasma or in an area in proximity to the plasma from plasma emitted light for a detection purpose, it is possible to substantially increase the sensitivity of detection to detect foreign particle on the order of down to sub-microns floating in the plasma or in an area in proximity to the plasma. As a result, there is exhibited an effect that it is possible to carry out in-situ monitoring of a state of pollution in a plasma processing chamber in a real-time manner and to reduce the number of inadvertently produced bad products due to foreign particle stuck thereto, allowing semiconductor devices with a high quality to be manufactured at a high yield.

In addition, according to the present invention, by using a diffractionless beam, it is possible to scan the diffractionless beam in an area in proximity to the entire surface of a substrate to be processed at a uniform radiation of energy and a detection with uniform sensitivity. Furthermore, by separating weak scattered lights emanating from foreign particle on the order of down to sub-microns floating in a plasma or in an area in proximity to the plasma from plasma emitted light for a detection purpose, it is possible to substantially increase the sensitivity of detection to detect foreign particle on the order of down to sub-microns floating in the plasma or in an area in proximity to the plasma at the entire surface of the substrate. As a result, there is exhibited an effect that it is possible to carry out in-situ, real-time monitoring of a state of pollution in a plasma processing chamber and to reduce the number of inadvertently produced bad products due to foreign particle stuck thereto, allowing semiconductor devices with a high quality to be manufactured at a high yield.

Moreover, according to the present invention, by separating weak back-scattered lights emanating from foreign particle on the order of down to sub-microns floating in a plasma or in an area in proximity to the plasma from plasma emitted light for a detection purpose, the laser radiating optical system and the scattered-light detecting optical system can be made compact as well as it makes easy to prevent an observation window from being stuck with foreign particles, and the sensitivity of detection to detect foreign particle on the order of down to sub-microns floating in the plasma or in an area in proximity to the plasma can be increased substantially. As a result, there is exhibited an effect that it is possible to carry out in-situ, real-time monitoring of a state of pollution in a plasma processing chamber and to reduce the number of inadvertently produced bad products due to foreign particles stuck thereto, allowing semiconductor devices with a high quality to be manufactured at a high yield.

Moreover, the present invention exhibits an effect of an ability to know a time to clean the plasma processing apparatus with a high degree of accuracy.

In addition, according to the present invention, the frequency of preventive work to check foreign particle by using a dummy wafer can be reduced to give rise to effects of cost reduction and productivity improvement.

Furthermore, the present invention exhibits an effect of possible automation of the entire manufacturing line.

What is claimed is:

1. A semiconductor manufacturing method comprising the steps of:

providing a semiconductor substrate in a processing chamber;

generating a plasma in the processing chamber;

manufacturing a semiconductor substrate by carrying out processing on the semiconductor substrate by the generated plasma in the processing chamber;

detecting a foreign particle floating within one of the generated plasma and an area in proximity thereto in the processing chamber including the steps of radiating an intensity-modulated light, into the processing chamber through a radiation window provided on a wall of the processing chamber;

optically receiving a light obtained from the processing chamber through an observation window provided on the wall of the processing chamber, by a detector, and converting the received light into a first signal;

obtaining information of the floating foreign particle, by extracting from the first signal a signal component having a frequency which is the same as that of the intensity-modulated light; and taking the manufactured semiconductor substrate outside from the processing chamber.

2. A semiconductor manufacturing method according to claim 1, wherein the intensity-modulated light is modulated at a frequency which is different from an excitation frequency of the plasma and its high-order frequencies.

3. A semiconductor manufacturing method according to claim 1, wherein the intensity-modulated light is modulated at a frequency which is different from an emission frequency of the generated plasma and its high-order frequencies.

4. A semiconductor manufacturing method according to claim 1, wherein the step of carrying out processing comprises the step of forming a film on the semiconductor substrate by the generated plasma.

5. A semiconductor manufacturing method according to claim 1, wherein the step of carrying out processing comprises the step of etching the semiconductor substrate by the generated plasma.

6. A semiconductor manufacturing method according to claim 1, wherein the radiation window is the same as the observation window.

7. A semiconductor manufacturing method according to claim 1, further comprising the step of diagnosing a state of pollution on the semiconductor substrate or in the processing chamber, in accordance with the obtained information of the floating foreign particle.

8. A semiconductor manufacturing method according to claim 7, further comprising the step of removing the manufactured semiconductor from a semiconductor manufacturing line in accordance with the result of diagnosing of the state of pollution.

9. A semiconductor manufacturing method according to claim 7, further comprising the step of controlling cleaning of the processing chamber in accordance with the result of diagnosing of the state of pollution.

10. A semiconductor manufacturing method according to claim 1, wherein the step of radiating the intensity-modulated light includes a step of scanning said radiated intensity-modulated light along a surface of the semiconductor substrate.

11. A plasma processing method comprising the steps of:

providing a semiconductor substrate in a processing chamber;

generating a plasma in the processing chamber;

carrying out processing on the semiconductor substrate by the generated plasma in the processing chamber;

detecting a foreign particle floating within one of the generated plasma and an area in proximity thereto in the processing chamber including a step of radiating an intensity-modulated light into the processing chamber through a radiation window provided on a wall of the processing chamber;

optically receiving a light obtained from the processing chamber through an observation window provided on the wall of the processing chamber, by a detector and converting the received light into a first signal;

obtaining information of the floating foreign particle by extracting from the first signal a signal component having a frequency which is the same as that of the light intensity-modulated; and taking the semiconductor substrate outside from the processing chamber.

12. A plasma processing method according to claim 11, wherein the intensity-modulated light is modulated at a frequency which is different from an excitation frequency of the plasma and its high-order frequencies.

13. A plasma processing method according to claim 11, wherein the intensity-modulated light is modulated at a frequency which is different from an emission frequency of the plasma and its high-order frequencies.

14. A plasma processing method according to claim 11, wherein the step of carrying out processing comprises the step of forming a film on the semiconductor substrate by the reaction of the generated plasma.

15. A plasma processing method according to claim 11, wherein the step of carrying out processing comprises the step of etching the semiconductor substrate by the reaction of the generated plasma.

16. A semiconductor manufacturing method according to claim 11, wherein the step of radiating the intensity-modulated light includes a step of scanning said radiated intensity-modulated light along a surface of the semiconductor substrate.

17. A semiconductor manufacturing method comprising the steps of:

providing a semiconductor substrate in a processing chamber;

generating a plasma in the processing chamber;

manufacturing a semiconductor substrate by carrying out processing on the semiconductor substrate by the generated plasma in the processing chamber;

detecting a foreign particle floating within one of the generated plasma and an area in proximity thereto in the processing chamber including a step of radiating an intensity-modulated light into the processing chamber through an observation window provided on a sidewall of the processing chamber;

optically receiving through the observation window a light from the processing chamber which includes scattered light generated from the floating foreign particle by a detector and converting the received light into a first signal;

obtaining information of the floating foreign particle by extracting from the first signal a signal component corresponding to the scattered light generated from the floating foreign particle; and taking the manufactured semiconductor substrate outside from the processing chamber.

18. A semiconductor manufacturing method according to claim 17, wherein the step of radiating the intensity-modulated light includes a step of scanning said radiated intensity-modulated light along a surface of the semiconductor substrate.

19. A semiconductor manufacturing method comprising the steps of:

providing a semiconductor substrate in a processing chamber;

generating a plasma in the processing chamber;

manufacturing a semiconductor substrate by carrying out processing on the semiconductor substrate by the generated plasma in the processing chamber;

detecting a foreign particle floating within one of the generated plasma and an area in proximity thereto in the processing chamber including a step of radiating an intensity-modulated light into the processing chamber through a radiation window provided on a wall of the processing chamber;

optically receiving a light from the processing chamber, which includes back scattered light generated in a backward direction to the radiation direction from the floating foreign particle, through an observation window provided on the wall of the processing chamber by a detector and converting the received light into a first signal;

obtaining information of the floating foreign particle by extracting from the first signal a signal component corresponding to the back scattered light generated in the backward direction from the floating foreign particle without being influenced by the plasma; and taking the manufactured semiconductor outside from the processing chamber.

20. A semiconductor manufacturing method according to claim 19, wherein the radiation window is the same as the observation window.

21. A semiconductor manufacturing method according to claim 19, wherein an optical axis of the light radiated into the processing chamber is coincident with an optical axis of the light received from the processing chamber.

22. A semiconductor manufacturing method according to claim 19, wherein the step of radiating the intensity-modulated light includes a step of scanning said radiated intensity-modulated light along a surface of the semiconductor substrate.

* * * * *